United States Patent [19]
Von Der Osten et al.

[11] Patent Number: 5,858,757
[45] Date of Patent: Jan. 12, 1999

[54] STABILIZED ENZYMES AND DETERGENT COMPOSITIONS

[75] Inventors: Claus Von Der Osten; Sven Branner, both of Lyngby; Allan Svendsen, Birkeroed; Lisbeth Hedegård, Copenhagen; Nina Eriksen, Frederiksberg, all of Denmark; Maarten Robert Egmond, Linschoten, Netherlands; Eric Casteleijn, Capelle a/d Ijssel, Netherlands

[73] Assignee: Novo Nordisk A/S, Bagsvaerd, Denmark

[21] Appl. No.: 140,083

[22] PCT Filed: Apr. 30, 1992

[86] PCT No.: PCT/DK92/00138

§ 371 Date: Nov. 11, 1993

§ 102(e) Date: Nov. 11, 1993

[87] PCT Pub. No.: WO92/19729

PCT Pub. Date: Nov. 12, 1992

[30] Foreign Application Priority Data

May 1, 1991 [EP] European Pat. Off. ............ 91610036

[51] Int. Cl.⁶ .................. C12N 9/54; C12N 15/11; C12N 15/57; C12N 15/75
[52] U.S. Cl. .................. 435/221; 435/222; 435/220; 435/69.1; 435/320.1; 435/252.3; 435/252.31; 536/23.2; 935/14; 935/29; 935/74
[58] Field of Search .................. 435/220, 221, 435/222, 69.1, 252.3, 320.1; 536/23.2

[56] References Cited

U.S. PATENT DOCUMENTS

| | | | |
|---|---|---|---|
| 4,980,288 | 12/1990 | Bryan et al. | 435/222 |
| 5,185,258 | 2/1993 | Caldwell et al. | 435/220 |
| 5,324,653 | 6/1994 | Van Eekelen | 435/221 |
| 5,336,611 | 8/1994 | Van Eckelen et al. | 435/221 |
| 5,340,735 | 8/1994 | Christianson et al. | 435/221 |

FOREIGN PATENT DOCUMENTS

| | | |
|---|---|---|
| 0236040 | 9/1989 | European Pat. Off. |
| WO 8705050 | 8/1987 | WIPO |
| WO 8901520 | 2/1989 | WIPO |
| WO 89/09819 | 10/1989 | WIPO |
| 9100345 | 1/1991 | WIPO |

OTHER PUBLICATIONS

Piela et al., Biopolymers, vol. 26, pp. 1587–1600 (1987).
Balajai et al., Biochem. Biophys. Research Comm. vol. 160, No. 1, 109–14 (1989).
Wells et al., Nucleic Acids Research, vol. 11, No. 22, pp. 7911–925 (1983).
Jany et al., Biol. Chem. Hoppe–Seyler, vol. 366, pp. 485–492 (1985).
Meloun et al., FEBS Letters 2463, vol. 183, No. 2, pp. 195–200 (1985).
Svendsen et al., FEBS Letters 3361, vol. 196, No. 2, pp. 228–232 (1986).
Nedkov et al., Biol. Chem. Hoppe–Seyler, vol. 366, pp. 421–430 (1985).
Jacobs et al., Nucleic Acid Research, vol. 13, No. 24, pp. 8913–8926.
Vasantha et al., J. Bacteriology, vol. 159, No. 3, pp. 811–819 (1984).

(List continued on next page.)

*Primary Examiner*—Robert A. Wax
*Assistant Examiner*—William W. Moore
*Attorney, Agent, or Firm*—Steve T. Zelson; James J. Harrington

[57] ABSTRACT

The invention relates to stabilized subtilisin proteases wherein one or more prolines is substituted for a native amino acid at stabilizing positions defined both by the range of the dihedral angles in the primary structure present at the substitution site and by selected characteristics of the protease secondary structure in the vicinity of the substitution site, to nucleotide sequences that encode the stabilized proteases, and to host organisms that contain the nucleotide sequences encoding the stabilized proteases.

19 Claims, 20 Drawing Sheets

OTHER PUBLICATIONS

Kurihara et al., J. Biological Chem., vol. 247, No. 17, pp. 5619–5631 (1985).

Priest, Bacteriological Reviews, vol. 41, No. 3, pp. 711–753 (1977).

White et al. Principles of Biochemistry, Fifth Edition, pp. 271–272 (1973).

Takagi, H., et al., 1989, Journal of Biochemistry, 105(6): 953–956.

Wu, H. et al., 1990, Proceedings of the National Academy of Sciences, U.S.A., 87:5888–5892.

Estink, M.R., et al., 1990, Proceedings of the SPIE International Society of Optical Engineers, 10241(2Pt.1): 137–143.

```
                                                    A                                                                 E                                                        B
                                                    l                                                                 c                                                        g
                                                    w                                                                 o                                                        l
                                                    N                                                                 R                                                        I
                                                    I                                                                 V                                                        I                   120
     ..00  TTGACAGGTTTCTGG|GTAAAAGTTGCTGTCCTGATACAGGGATA|TCCACTCATCCAGAT
   61.     ----+----|----+----|----+----|----+----|----+----|----+----|
           AACTGTCCAAGACCACATTTT|AACGACAGGAGCTATGTCCCTATAGGTGA|GTAGGTCTA
                                                                                            T   H   P   D     —
           L   T   G   S   G   V   K   V   A   V   L   D   T   G   I   S   H   P   D
                                                                                        35  37              41

S                                                   H                                                   S
              s                                                   i                                                   a
              p                                                   n                                                   c
           A4-00 I                                                d                                                   l
                                                                  I                                                   c
                                                                  I                            B1-00 II
                                                                  I                                                   II                                                       180
           CTAAATATTCGTGGTGGCGC|AAGCTTTGTACCAGGGAACCGTCGACTCAAGATGG|AAT
   121     ----+----|----+----|----+----|----+----|----+----|----+----|
           GATTTATAAGCACCACCGCGTTCGA|AACATGGTCCCCTTGGCAGCTGAGTTCTACCCTTA
                                                                                                                      N
           L   N   I   R   G   G   A   S   F   V   P   G   E   P   S   T   Q   D   G   N
                                                                                        55  57              62
```

Fig. 1B

```
                                         P  D
                                         v  r
                                         u  a
                                         I  I
              B2-00                                     B3-00
     GGGCATGGCACGCGGGACCCGGGACGATC GCTGCTTTAAACAATTCGATTGGCGTTCTT
181  ---+----+----+----+----+----+----+----+----+----+----+----  240
     CCGGTACCGTGCCGTACACCGGGCCCTGCTAGCGACGAAA TTGTTAAGCTAACCGCAAGAA

G  H  G  T  H  V  A  G  T  I  A  A  L  N  N  S  I  G  V  L
                                                                    82

E  B                                 T
           c  p                                 a
           o  u                                 q
           4  1                                 I  I
           7  1                                 I  I
           I  0                                 I  I
           I  2                                 I  I
                                  A
                                  v
                                  r
                                  I
                                  I
                              B4-00                                       B5-
     GGC GTAGCTCCTAGCGCTGAGCTATACGCTGTTAAAGTC CTAGGGGCGAGCCGGTTCAGGT
241  ---+----+----+----+----+----+----+----+----+----+----+----  300
     CCGCATCGA GATCGCGACTCGATATGCGACAATTTCAGGATCCCCG CTCGCCAAGTCCA

```
     PflMI
                                                                SphI
   TCGGTCAGCTCGATT GCCCAAGGATTGGAATGGGCAGGAACAATGGCATG CACGTTGCT
                                          B6-00
-00 ----+----|----+----|----+----|----+----|----+----|----+---- 360
   AGCCAGTCGAGCTAA CGGGTT CCTAACCTTACCCGTCCCTTGTTACC GTACGTGCAACGA

S   V   S   S   I   A   Q   G   L   E   W   A   G   N   N   G   M   H   V   A   -
                                                                              122
           XmnI                           XhoI
                                    C1-00            C2-00
     AATTTGAGTTTAGGAAGCCCTTCG CCAAGTGCCACACTCGAGCAAGCTGTTAATAGCCG
361  ----+----|----+----|----+----|----+----|----+----|----+---- 420
     TTAAACTCAAATCCTTCGGGAAGC GGTTCACGGTGTGAGCTCGTTCGACAATTATCGGC

```
            Xba I        C3-00                                  Eco RI           D1-00
     421  ACTTCTAGAGGCGGTTCTTGTTGTAGCGGGCATCTGGAATTCAGGTGCAGGCTCAATCAGC  480
          --------+---------+---------+---------+---------+---------+
          TGAAGATCTCCGCAAGAACAACATCGCCCGTAGACCCTTAAGTCCACGTCCGAGTTAGTCG

T  S  R  G  V  L  V  V  A  A  S  G  N  S  G  A  G  S  I  S
           158                                                        163
                Bss M                                          B
                 H  m                                          c
                 II e                                          l
                    I                                          I
     481  TATCCGGCGCGCTATGCGAACGCAATGGCAGTCGGAGCTACTGATCAAAAACAACAACCGC  540
          --------+---------+---------+---------+---------+---------+
          ATAGGCCGCGCGATACGCTTGCGTTACCGTCAGCCTCGATGACTAGTTTTTGTTGTTGGCG
                           D2-00

```
        Xm                                      Hgi
        NaI                                     EII
                  E1-00                             E2-00
      .GTTGCAGGTGCGGCCGCC|TTGTTAAACAAAAGAACCCATCTTGGTCTAATGTACAA|ATT
661   ----+---------+----.----+---------+---------+---------+----  720
       CAACGTCCACGCCGGCGGGGAACAA|TTTGTTTTCTTGGGTAGAACCAGATTACATGTTTAA
                                Nsp
        V  A  G  A  A  A  L  V  K  Q  K  N  P  S  W  S  N  V  Q  I   246

Spe
                                      I                E4-00
       CGAAATCATCTAAAGAATACGGCAACTAGTTTA|GGAAGCACGAACTTGTATGGAAGCGGA
721   ----+---------+---------+---------+---------+---------+----  780
       GCT|TAGTAGATTTCTTATGCCGTTGATCAAATCCTTCGTGC|TTGAACATACCTTCGCCT
          E3-00
        R  N  H  L  K  N  T  A  T  S  L  G  S  T  N  L  Y  G  S  G   266
```

Fig. 1G

Enzymes that do cut:

| | | | | | |
|---|---|---|---|---|---|
| AccI | AflIII | AlwNI | AvaI | AvrII | BamHI | | |
| BglII | Bpu1102I | BsgI | BsiEI | Bspl286I | BspMI | BanI | BclI |
| BstYI | ClaI | DraI | DsaI | EaeI | Eco47III | BssHII | BstXI |
| FsiI | GdiII | HaeI | HaeII | HgiAI | HgiEII | EcoRI | EcoRV |
| HpaI | KpnI | MluI | MmeI | MslI | NcoI | HincII | HindIII |
| NotI | NspI | NspV | NspBII | PflMI | PvuI | NdeI | NheI |
| SmaI | SpeI | SphI | SspI | StuI | StyI | PvuII | SalI |
| XbaI | XhoI | XmaIII | XmnI | | | TaqII-1 | Tth111I |

Fig. 1I

Enzymes that do not cut:

| | | | | | | |
|---|---|---|---|---|---|---|
| AatII | AflII | AgeI | ApaI | ApaBI | ApaLI | AscI | AseI |
| BaeI | BalI | BanII | BbsI | BcgI | BcgI | BetI | BglI |
| Bpu10I | BsaI | BsaAI | BsaBI | BsaHI | BsiI | BsiWI | BsmI |
| BspEI | BspGI | BspHI | Bst1107I | BstEII | Bsu36I | CfrI0I | DraIII |
| DrdI | DrdII | Eam1105I | EarI | EciI | Eco57I | EcoNI | EcoO109I |
| Esp3I | FseI | FspI | GsuI | MunI | NaeI | NarI | NruI |
| NsiI | PacI | Pfl1108I | PmeI | PmlI | PpuMI | PshAI | PstI |
| RleAI | RsrII | SacII | SapI | ScaI | SfcI | SfiI | SgrAI |
| SnaBI | Sse8387I | SstI | SwaI | TaqII-2 | Tth111I | XcmI | |

Fig. 1J

```
         KpnI  PstI EcoRI Hind3  ClaI    SphI BamHI
5'-AATTGGTACCCTGCAGGAATTCAAGCTTATCGATGGCATGCGGATCC-3'
        . .    .     .    .  .     .    .      .
3'-CCATGGGACGTCCTTAAGTTCGAATAGCTACCGTACGCCTAGGTCGA-5'
```

Fig. 1M

STABILIZED ENZYMES AND DETERGENT COMPOSITIONS

TECHNICAL FIELD

This invention relates to novel stabilized proteases, nucleotide sequences encoding the stabilized proteases, and host organisms containing the nucleotide sequences encoding the novel stabilized proteases.

BACKGROUND ART

Proteases/Subtilisins

Proteases, or (interchangeably) peptidases, are enzymes that cleave the amide linkages in protein substrates. Bacteria of the Bacillus species secrete two extracellular species of protease, a neutral or metalloprotease, and an alkaline protease which is functionally a serine endopeptidase, referred to as subtilisin.

A serine protease is an enzyme which catalyses the hydrolysis of peptide bonds, and in which there is an essential serine residue at the active site [White, Handler and Smith (1973); Principles of Biochemistry; Fifth Edition, McGraw-Hill Book Company, N.Y., 271–272].

The bacterial serine proteases have molecular weights in the range of 20,000 to 45,000. They hydrolyse simple terminal esters and are similar in activity to eukaryotic chymotrypsin, also a serine protease. A more narrow term, alkaline protease, covering a sub-group, reflects the high pH optimum of some of the serine proteases, from pH 9.0 to 11.0 [for review, see Priest; Bacteriological Rev., 41 711–753 (1977)].

In relation to the present invention a subtilisin is a serine protease produced by Gram-positive bacteria or fungi. According to another definition, a subtilisin is a serine protease, wherein the relative order of the amino acid residues in the catalytic triad is Asp—His—Ser (positions 32, 64, and 221). A wide variety of subtilisins has been identified, and the amino acid sequences of a number of subtilisins have been determined. These include among others six subtilisins from Bacillus strains, namely, subtilisin 168, subtilisin BPN', subtilisin Carlsberg, subtilisin DY, subtilisin amylosacchariticus, and mesentericopeptidase [Kurihara et al. (1972); J. Biol. Chem.; 247 5629–5631; Wells et al. (1983); Nucleic Acids Res.; 11 7911–7925; Stahl and Ferrari (1984); J. Bacteriol.; 159 811–819; Jacobs et al. (1985); Nucl. Acids Res.; 13 8913–8926; Nedkov et al. (1985); Biol. Chem. Hoppe-Seyler; 366 421–430; Svendsen et al. (1985); FEBS LETTERS; 196 228–232] one subtilisin from an actino-mycetales, Thermitase from *Thermoactinomyces vulgaris* [Meloun et al. (1985); FEBS LETTERS; 1983 195–200], and one fungal subtilisin, proteinase K from *Tritirachium album* [Jany and Mayer (1985); Biol. Chem. Hoppe-Seyler; 366 584–492].

Proteases such as subtilisins have found much utility in industry, particularly in detergent formulations, as they are useful for removing proteinaceous stains.

The Structure of Proteins

Proteases are globular proteins and quite compact due to the considerable amount of folding of the long polypeptide chain. The polypeptide chain essentially consists of the "backbone" and its "side-groups". As the peptide bond is planar, only rotations around the $C_a$—N axis and the $C_a$—C' axis are permitted. Rotation around the $C_a$—N bond of the peptide backbone is denoted by the torsion angle $\phi$ (phi), rotation around the $C_a$—C' bond by $\psi$ (psi) [vide e.g. Creighton, T. E. (1984); Proteins; W. H. Freeman and Company, New York]. The choice of the values of these angles of rotation is made by assigning the maximum value of +180° (which is identical to −180°) to the maximally extended chain. In the fully extended polypeptide chain, the N, $C_a$ and C' atoms are all "trans" to each other. In the "cis" configuration, the angles $\phi$ and $\psi$ are assigned the value of 0°. Rotation from this position around the bonds so that the atoms viewed behind the rotated bond move "counter-clockwise" is assigned negative values by definition, those "clockwise" are assigned positive values. Thus, the values of the torsion angles lie within the range −180° to +180°.

Since the $C_a$-atoms are the swivel point for the chain, the side-groups (R-groups) associated with the $C_a$-atoms become extremely important with respect to the conformation of the molecule.

The term "conformation" defines the participation of the secondary and tertiary structures of the polypeptide chains in moulding the overall structure of a protein. The correct conformation of a protein is of prime importance to the specific structure of a protein and contributes greatly to the unique catalytic properties (i.e. activity and specificity) of enzymes and their stability.

The amino acids of polypeptides can be divided into four general groups: nonpolar, uncharged polar, and negatively or positively charged polar amino acids. A protein molecule, when submerged in its aqueous environment in which it normally occurs, tends to expose a maximum number of its polar side-groups to the surrounding environment, while a majority of its nonpolar side groups is oriented internally. Orientation of the side-groups in this manner leads to a stabilization of protein conformation.

Proteins, thus, exist in a dynamic equilibrium between a folded and ordered state, and an unfolded and disordered state. This equilibrium in part reflects the short range interactions among the different segments of the polypeptide chain, which tends to stabilize the overall structure of proteins. Thermodynamic forces simultaneously tend to promote randomization of the unfolding molecule.

A way to engineer stabilized proteins is to reduce the extent of unfolding by decreasing the flexibility of the polypeptide backbone, and simultaneously decreasing the entropy of the unfolded chain. So far only few attempts have been made to implement this rationale in the development of novel stabilized proteases.

A general principle of increasing protein thermostability has been provided [Suzuki, Y. (1989); Proc. Japan Acad.; 65 Ser. B]. In this article Suzuki states that the thermostability of a globular protein can be enhanced cumulatively to a great extent by increasing the frequency of proline occurrence at the second site of β-turns without significant alterations in the secondary and tertiary structures as well as in the catalytic function of enzymes. The principle is based on various facts and findings, among these the fact that proline residues show a strong tendency to occur preferentially at the second site of β-turns [Levitt, M (1978); Biochemistry; 17 4277–4285; and Chou, P. Y. & Fasman, G. D. (1977); J. Mol. Biol.; 115 135–175]. The principle is restricted to insertion of proline into the second site of β-turns in proteins, no other sites are mentioned.

International Patent Publication WO 89/01520 (Cetus Corporation, USA) provides a method for increasing the stability of a protein by decreasing the configurational entropy of unfolding the protein. The method is applied on a *Streptomyces rubiqinosus* xylose isomerase, and it involves substitution of an amino acid with proline, or replacement of glycine with alanine, at predicted substitution sites.

In International Patent Publication WO 89/09819 (Genex Corporation, USA) a method for combining mutations for stabilization of subtilisins is provided. This publication lists a number of amino acid mutations that have been found to be thermally stabilizing mutations. The list comprises substitution of serine with proline at position 188 of subtilisins (BPN' numbering).

International Patent Publication WO 87/05050 (Genex Corporation, USA) describes a method for mutagenesis and screening. By this method one or more mutations are introduced by treatment with mutagenizing agents, and the method includes subsequent screening for products with altered properties. As a result of this random mutagenesis a subtilisin with a proline residue at position 188 (BPN' numbering) is provided.

It is an object of this invention to provide novel proteases having improved stability.

SUMMARY OF THE INVENTION

The present invention provides novel stabilized proteases, in which a naturally occurring amino acid residue (other than proline) has been substituted with a proline residue at one or more positions, at which position(s) the dihedral angles $\phi$ (phi) and $\psi$ (psi) constitute values within the intervals $[-90°<\phi<-40°$ and $-180°<\psi<180°]$, preferably within the intervals $[-90°<\phi<-40°$ and $120°<\psi<180°]$ or $[-90°<\phi<-40°$ and $-50°<\psi<10°]$, and which position(s) is/are not located in regions, in which the protease is characterized by possessing $\alpha$-helical or, $\beta$-sheet structure.

In another aspect, the invention relates to nucleotide sequences encoding the proteases. In further aspects, the invention relates to an expression vector comprising a nucleotide sequence encoding a protease, and to a host organism containing this expression vector.

Subtilisins

In the context of this invention a subtilisin is defined as a serine protease produced by gram-positive bacteria or fungi. According to another definition, a subtilisin is a serine protease, wherein the relative order of the amino acid residues in the catalytic triad is Asp—His—Ser (positions 32, 64, and 221, BPN' numbering).

Amino Acids

As abbreviations for amino acids the following symbols are used:

| A | = | Ala | = | Alanine |
|---|---|-----|---|---------|
| C | = | Cys | = | Cysteine |
| D | = | Asp | = | Aspartic acid |
| E | = | Glu | = | Glutamic acid |
| F | = | Phe | = | Phenylalanine |
| G | = | Gly | = | Glycine |
| H | = | His | = | Histidine |
| I | = | Ile | = | Isoleucine |
| K | = | Lys | = | Lysine |
| L | = | Leu | = | Leucine |
| M | = | Met | = | Methionine |
| N | = | Asn | = | Asparagine |
| P | = | Pro | = | Proline |
| Q | = | Gln | = | Glutamine |
| R | = | Arg | = | Arginine |
| S | = | Ser | = | Serine |
| T | = | Thr | = | Threonine |
| V | = | Val | = | Valine |
| W | = | Trp | = | Tryptophan |
| Y | = | Tyr | = | Tyrosine |
| B | = | Asx | = | Asp (D) or Asn (N) |
| Z | = | Glx | = | Glu (E) or Gln (Q) |
| X | = | an arbitrary amino acid | | |
| * | = | deletion or absent amino acid | | |

Protease Variants

A stabilized protease of this invention is a protease variant or mutated protease. By a protease variant or mutated protease is meant a protease obtainable by alteration of a DNA nucleotide sequence of the parent gene or its derivatives. The protease variant or mutated protease may be expressed and produced when the DNA nucleotide sequence encoding the protease is inserted into a suitable vector in a suitable host organism. The host organism is not necessarily identical to the organism from which the parent gene originated.

Amino Acid Numbering

In the context of this invention a specific numbering of amino acid residue positions in subtilisins is employed. By alignment of the amino acid sequences of various subtilisins along with subtilisin BPN', it is possible to allot a number to the amino acid residue position in any subtilisin to the number of the analogous amino acid position in subtilisin BPN' ("BPN' numbering", vide e.g. International Patent Publications Nos. WO 89/06279 and WO 91/00345).

In describing the various protease variants produced or contemplated according to the invention, the following nomenclatures were adapted for ease of reference:

[Original amino acid; Position; Substituted amino acid]

Accordingly, the substitution of alanine with proline in position 195 is designated as:

A195P

Deletion of an aspartic acid at position 36 is indicated as: D36*, and an insertion in such a position is indicated as: 36D for insertion of an aspartic acid in position 36.

Multiple mutations are separated by plusses, i.e.:

A194P+G195E representing mutations in positions 194 and 195 substituting alanine with proline and glycine with glutamic acid, respectively.

If a substitution is made by mutation in e.g. subtilisin 309, the product is designated e.g. "subtilisin 309/G195E".

All positions mentioned in this context refer to the BPN' numbers described above.

Proteolytic Activity

In the context of this invention proteolytic activity is expressed in Kilo NOVO Protease Units (KNPU). The activity is determined relatively to an enzyme standard (SAVINASE™), and the determination is based on the digestion of a dimethyl casein (DMC) solution by the proteolytic enzyme at standard conditions, i.e. 50° C., pH 8.3, 9 min. reaction time, 3 min. measuring time. A folder AF 220/1 is available upon request to Novo Nordisk A/S, Denmark, which folder is hereby included by reference.

Wash Performance

The ability of an enzyme to catalyse the degradation of various naturally occurring substrates present on the objects to be cleaned during e.g. wash is often referred to as its washing ability, washability, detergency, or wash performance. Throughout this application the term wash performance will be used to encompass this property.

BRIEF DESCRIPTION OF DRAWINGS

The present invention is further illustrated by reference to the accompanying drawings, in which.

DETAILED DISCLOSURE OF THE INVENTION

Figure 1A:
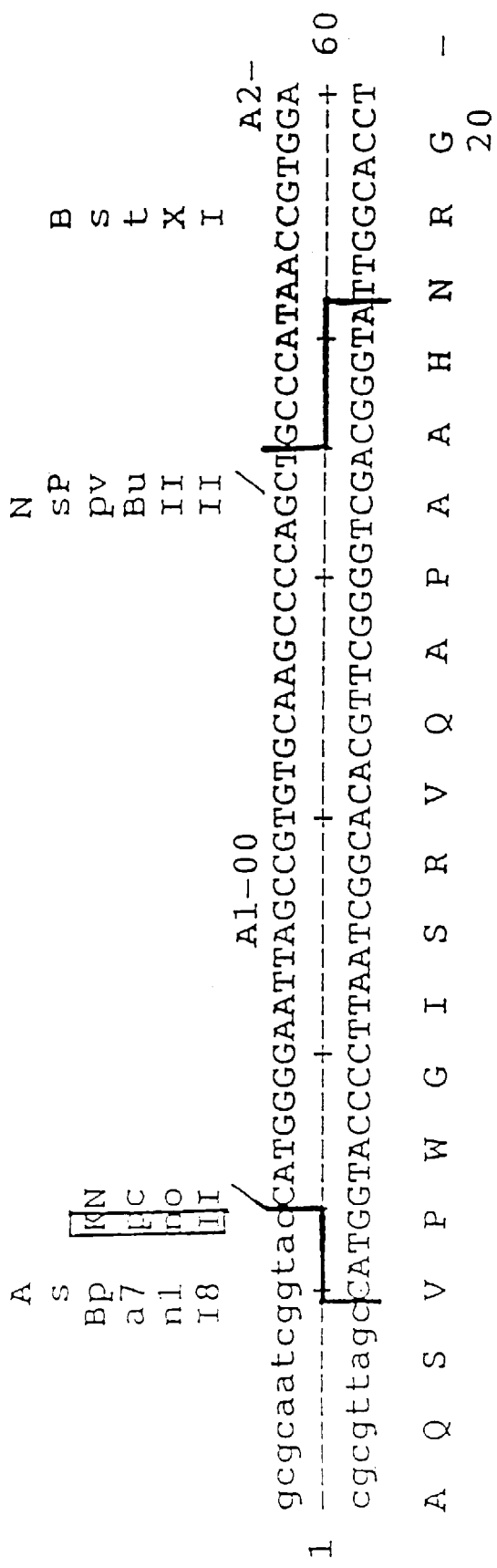
FIG. 1 (sheets 1/20–15/20) shows the construction of a synthetic gene.

The present invention provides novel stabilized proteases, in which a naturally occurring amino acid residue (other than proline) has been substituted with a proline residue at one or more positions, at which position(s) the dihedral angles φ (phi) and ψ (psi) constitute values in the intervals [−90°<φ<−40° and −180°<ψ<180°], preferably the intervals [−90°<φ<−40° and 120°<ψ<180°] or [−90°φ<−40° and −50°<ψ<10°], and which position(s) is/are not located in regions, in which the protease is characterized by possessing α-helical or β-sheet structure.

In the context of this invention, a stabilized protease is a protease variant or mutated protease, being functionally equivalent or having structural features similar to a naturally occurring protease, and in which protease a naturally occurring amino acid residue (other than proline) has been substituted with a proline residue at one or more positions, at which position(s) the dihedral angles φ (phi) and ψ (psi) constitute values within the intervals [−90°<φ<−40° and −180°<ψ<180°], preferably the intervals [−90°<φ<−40° and 120°<ψ<180°] or [−90°<φ<−40° and −50°<ψ<10°], and which position(s) is/are not located in regions, in which the protease is characterized by possessing α-helical or β-sheet structure.

Moreover, in the context of this invention, a stabilized protease is a protease having improved stability, e.g. in respect to thermal stability, storage stability, etc., when compared to the parent enzyme.

Defining Secondary Structure of Proteins

The stabilized proteases of the invention may be obtained by subjecting the protease in question to analysis for secondary structure, identifying residues in the protease having dihedral angles φ (phi) and ψ (psi) confined to the intervals [−90°<φ<−40° and −180°<ψ<180°], preferably the intervals [−90°<φ<−40° and 120°<ψ<180°] or [−90°<φ<−40° and −50°<ψ<10°], excluding residues located in regions in which the protease is characterized by possessing α-helical or β-sheet structure, if a proline residue is not already at the identified position(s), substitution of the naturally occurring amino acid residue with a proline residue at the identified position(s), preferably by site directed mutagenesis applied on a gene encoding the protease in question, and gene expression by insertion of the gene encoding the stabilized protease in a suitable host organism, followed by cultivation of said host organism in a suitable nutrient medium, and recovery of the desired protease.

This preparation includes subjecting the protease in question to analysis for secondary structure. To perform such analysis the atomic structure of the protease has to be elucidated. The atomic structure can be determined by X-ray diffraction techniques. X-ray diffraction techniques are described by e.g. Hendrickson, W. A. [X-ray diffraction; in Protein Engineering (Ed: Oxender, D. L. and Fox, C. F.), ch. 1; Alan R. Liss, Inc. (1987)] and Creighton, T. E., supra, ch. 6.

The crystal structure of Subtilisin 309 has been deduced [vide Beizel, B., Klupsch, S., Papendorf, G., Hastrup, S., Branner, S., and Wilson, K.S. (1992); J. Mol. Biol. 223 427–445], and the coordinates have been deposited and are available from the Brookhaven Protein Data Bank [Bemstein et al. (1977); J. Mol. Biol. 112 535–542].

When the atomic structure has been determined, it is possible to compute dihedral angles from the atomic coordinates. Moreover, it is possible to assign secondary structure elements. The secondary structure elements are defined on the basis of hydrogen bindings. Cooperative secondary structure is recognized as repeats of the elementary hydrogen-bonding patterns "turn" and "bridge". Repeating turns are "helices", repeating bridges are "ladders", connected ladders are "sheets".

Analysis for secondary structure elements requires a computerized compilation of structure assignments and geometrical features extracted from atomic coordinates. The conventional method to elucidate the secondary structure of a protein, based on its atomic coordinates, is described by Kabsch, W. and Sander, C. [Biopolymers (1983) 22 2577–2637]. In this article an algorithm for extracting structural features from the atomic coordinates by a pattern-recognition process is provided. First, H-bonds are identified based on electrostatic interactions between pairs of H-bonding groups. Next, the patterns of H-bonding are used to define secondary structure elements such as turns M, bends (S), bridges (B), helices (G,H,I), β-ladders (E) and β-sheets (E).

A computer program DSSP (Define Secondary Structure of Proteins), enabling the computation of Kabsch & Sander files and written in standard PASCAL, is available from the Protein Data Bank, Chemistry Dept., Brookhaven National Laboratory, Upton, N.Y. 11973.

After the dihedral angles φ (phi) and ψ (psi) for the amino acids have been calculated, based on the atomic structure in the crystalline proteases, it is possible to select position(s) which has/have dihedral phi and psi angles favourable for substitution with a proline residue. The aliphatic side chain of proline residues is bonded covalently to the nitrogen atom of the peptide group. The resulting cyclic five-membered ring consequently imposes a rigid constraint on the rotation about the N—$C_a$ bond of the peptide backbone and simultaneously prevents the formation of hydrogen bonding to the backbone N-atom. For these structural reasons, prolines are generally not compatible with α-helical and β-sheet secondary conformations. Due to the same rotational constraint about the $C_a$—N bond, and due to the requirement that neighbouring amino acids in the chain are not perturbed, the magnitudes of the dihedral angles phi and psi (and in particular phi) are confined to limited intervals for proline residues in polypeptides. The dihedral angles for proline residues in polypeptides are almost exclusively within the intervals [−90°<φ<−40° and −180°<ψ<180°], preferably the intervals [−90°<φ<−40° and 120°<ψ<180°] or [−90°<φ<−40° and −50°<ψ<10°]. In this context, both cis- and trans-proline residues are considered.

A proline residue may already occur at one or more positions pointed out by the procedure described above, and then a substitution is, of course, irrelevant. Otherwise, the method includes substitution of the naturally occurring amino acid residue with a proline residue.

However, a substitution into proline at every of the predicted positions may not always bring about improved thermostability of the protease. At some of the positions revealed by this method, a substitution of a naturally occurring amino acid residue into a proline residue may even cause destabilisation due to unpredictable factors, such as loss of essential flexibility, loss of H-bond possibilities, unpredictable sterical hindrance, etc. Such "critical sites" are not to be foreseen.

It is to be expected that the stabilizing (or destabilizing) effects of individual substitutions are additive, vide e.g. Wells, J. A. [Biochemistry (1990) 29 (37) 8510–8517] and Table 4, below.

If a subtilisin different from subtilisin 309 is subjected to this method (although the two subtilisins may seem very much similar), not necessarily the same number of positions, nor particularly the identical positions, may result from the method. It is likely that some of the positions may be identical, and it is likely that the numbers of positions are of equal magnitude, but it is not to be foreseen.

However, it seems likely that the stabilizing proline substitutions resulting from the above described method, applied to any specific protease, may also have a stabilizing effect on any other protease, independent of the result of the above described method applied to such a protease.

When performing the method on a subtilisin 309 molecule (vide International Patent Application No. PCT/DK88/00002), a set of data as listed in Tables 1 and 2 can be obtained. Table 1 depicts a set of positions that—with respect to phi and psi angles—meet one criterion, and Table 2 depicts an additional set of positions that meet another criterion.

TABLE 1

Proline Mutants Proposed in Subtilisin 309 Based on phi and psi Angles.

Criteria: −90° < phi < −40° and 120° < psi < 180°, or
−90° < phi < −40° and −50° < psi < 10°.
Neither part of an alpha helix nor a beta sheet structure.

| BPN' numbers | phi angle | phi angle | Amino acid | Struc- ture | Mutant & Comments |
|---|---|---|---|---|---|
| 5 | −59 | 148 | P | | Pro already in Subt.309 |
| 11 | −80 | −1 | V | T | |
| 19 | −85 | 1 | R | T | |
| 24 | −57 | 132 | S | T | |
| 33 | −79 | 10 | T | S | |
| 37 | −89 | 145 | S | | |
| 38 | −58 | 146 | T | | |
| 40 | −60 | −27 | P | T | Pro already in Subt.309 |
| 52 | −59 | 131 | P | T | Pro already in Subt.309 |
| 55 | −71 | −22 | P | | Pro already in Subt.309 |
| 57 | −90 | 167 | S | S | |
| 59 | −60 | 151 | Q | | |
| 74 | −57 | 141 | A | | |
| 75 | −67 | 148 | L | | |
| 83 | −81 | 173 | G | | |
| 84 | −72 | −35 | V | S | |
| 86 | −59 | −12 | P | T | Pro already in Subt.309 |
| 88 | −68 | 152 | A | | |
| 97 | −73 | 174 | G | | |
| 98 | −57 | −32 | A | T | |
| 99 | −67 | −12 | S | T | |
| 119 | −70 | 149 | M | | |
| 129 | −68 | −24 | P | S | Pro already in Subt.309 |
| 130 | −85 | 126 | S | S | |
| 131 | −63 | 156 | P | | Pro already in Subt.309 |
| 145 | −88 | 10 | R | T | |
| 147 | −86 | 134 | V | | |
| 153 | −74 | −20 | S | | |
| 156 | −82 | −11 | S | S | |
| 158 | −70 | 159 | A | | |
| 163 | −66 | 166 | S | | |
| 169 | −52 | −33 | A | T | |
| 170 | −66 | −21 | R | T | |
| 171 | −67 | 141 | Y | S | |
| 172 | −52 | −43 | A | T | |
| 173 | −79 | 1 | N | T | |
| 182 | −63 | −16 | Q | T | |
| 186 | −65 | 133 | R | B | |
| 187 | −65 | 151 | A | | |
| 188 | −64 | −27 | S | T | |
| 189 | −77 | −17 | F | T | |
| 191 | −69 | 151 | Q | | |
| 194 | −56 | 130 | A | T | |
| 210 | −53 | 155 | P | T | Pro already in Subt.309 |
| 239 | −58 | −25 | P | T | Pro already in Subt.309 |
| 241 | −79 | 149 | W | | |
| 242 | −86 | 178 | S | | |
| 254 | −71 | 165 | A | S | |
| 256 | −59 | 136 | S | | |
| 259 | −48 | 131 | S | | |
| 265 | −69 | −20 | S | T | |

TABLE 1-continued

Proline Mutants Proposed in Subtilisin 309 Based on phi and psi Angles.

Criteria: −90° < phi < −40° and 120° < psi < 180°, or
−90° < phi < −40° and −50° < psi < 10°.
Neither part of an alpha helix nor a beta sheet structure.

| BPN' numbers | phi angle | phi angle | Amino acid | Struc- ture | Mutant & Comments |
|---|---|---|---|---|---|
| 267 | −79 | 127 | L | B | |
| 268 | −58 | 141 | V | | |

By relaxing the constraint on the psi angle relative to the criteria set up in Table 1, four additional mutants are proposed, vide Table 2.

TABLE 2

Proline Mutants Proposed in Subtilisin 309 based on phi and psi Angles.

Relaxed criteria: −90° < phi < −40 and −180° < psi < 180.
Neither part of an alpha helix nor a beta sheet structure.

| BPN' numbers | phi angle | psi angle | Amino add | Struc- ture | Mutant & Comments |
|---|---|---|---|---|---|
| 76 | −89 | 102 | N | S | |
| 125 | −90 | 67 | S | | |
| 160 | −83 | 27 | G | S | |
| 255 | −89 | 111 | T | B | |

Preferred Stabilized Proteases

Preferably, a protease of the invention is a stabilized subtilisin protease. In a more specific aspect, a preferred protease of the invention is a subtilisin, in which the stabilized subtilisin obtained is any subtilisin which comprises a substitution into a proline residue at one or more of the positions listed in Tables 1 and 2 (BPN' numbers), or positions analogous hereto.

In a more specific aspect, a proteases of the invention is a subtilisin in which a naturally occurring amino acid (other than proline) has been substituted with a proline residue at one or more of the positions: 38, 57, 98, 172, 188, 194, 242, and 259 (BPN' numbers). In further preferred embodiments, the subtilisin in addition comprises one or more of the following substitutions: 27R, 36D, 76D, 97N, 98R, 104Y, 120D, 128G, 195E, 206C, 218S, 235L, 235R, 237R, 251E, and 263F (BPN' numbers).

In a yet more specific aspect, the protease of the invention is a stabilized subtilisin 309, a stabilized subtilisin 147, a stabilized subtilisin BPN', or a stabilized subtilisin Carlsberg. Subtilisin 309 and Subtilisin 147 are variants of *Bacillus lentus* and described in U.S. Pat. No. 3,723,250 and International Patent Application PCT/DK88/00002, Subtilisin BPN' is described by Wells et al. [Nucleic Acids Res. (1983) 11 7911–7925]; Subtilisin Carlsberg is described by Smith et al. [Smith, E. L.; DeLange, R. J.; Evans, W. H.; Landon, W.; Markland, F. S. (1968); Subtilisin Carlsberg V. The complete sequence: comparison with subtilisin BPN'; Evolutionary relationships.; J. Biol. Chem. 243 (9) 2184–2191), and Jacobs et al. [Nucl. Acids Res. (1985) 13 8913–8926].

In another specific aspect, a protease of the invention is a stabilized subtilisin 309 in which one or more of the following substitutions have been introduced: T38P, S57P, A98P, S188P, A172P, A194P, S242P, and S259P (BPN' numbers). In further preferred embodiments, this subtilisin in addition comprises one or more of the following substitutions: K27R, *36D, N76D, G97N, A98R, V104Y, H120D, S128G, G195E, Q206C, N218S, K235L, K235R, K237R, K251E, and Y263F (BPN' numbers).

In yet another preferred embodiment, the protease of the invention is a subtilisin 309, in which one or more of the following substitutions have been introduced: T38P, S57P, A98P, A172P, A194P, S242P, and S259P (BPN' numbers). In a further preferred embodiment, this subtilisin 309 in addition comprises one or more of the following substitutions: K27R, *36D, N76D, G97N, A98R, V104Y, H120D, S128G, G195E, Q206C, N218S, K235L, K235R, K237R, K251E, and Y263F (BPN' numbers).

Most preferred proteases of the invention are: Subtilisin 309/K27R+*36D+G97N+A98R+A194P+K235R+K237R+K251E+Y263F, Subtilisin 309/K27R+*36D+G97N+A194P+K235R+K237R+K251E+Y263F, Subtilisin 309/K27R+*36D+G97N+A194P+K235R+K237R+Y263F, Subtilisin 309/*36D+N76D+H120D+A194P+G195E+K235L, Subtilisin 309/*36D+G97N+V104Y+H120D+A194P+G195E, Subtilisin 309/*36D+G97N+V104Y+H120D+A194P+G195E+K235L, Subtilisin 309/*36D+G97N+H120D+A194P+G195E, Subtilisin 309/*36D+G97N+H120D +A194P+G195E+K235L, Subtilisin 309/*36D+V104Y+H120D+A194P+G195E, Subtilisin 309/*36D+V104Y+H120D+A194P+G195E+K235L, Subtilisin 309/*36D +H120D+A194P+G195E, Subtilisin 309/*36D+H120D+A194P+G195E+K235L and Subtilisin 309/A194P (BPN' numbers).

The Effect of Proline Stabilization

The purified variants obtained according to this invention have been tested to wash at least equally well compared to the wild-type subtilisin (subtilisin 309), vide Example 5 for experimental data.

Figure 2A:
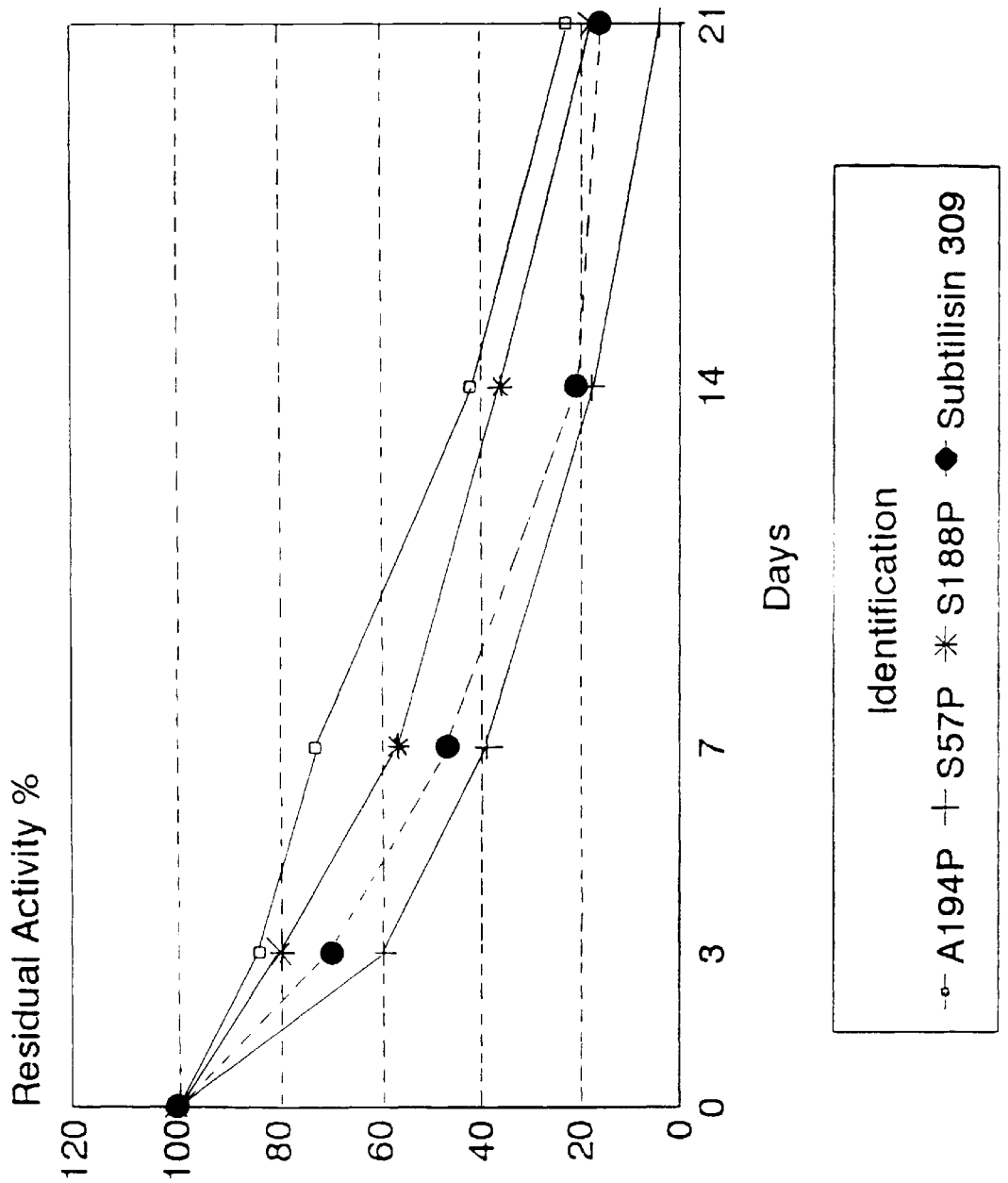
FIG. 2 (sheets 16/20–20/20) shows the residual activity of subtilisin 309 variants compared to wild type enzyme after storage in a liquid detergent.
Figure 2B:
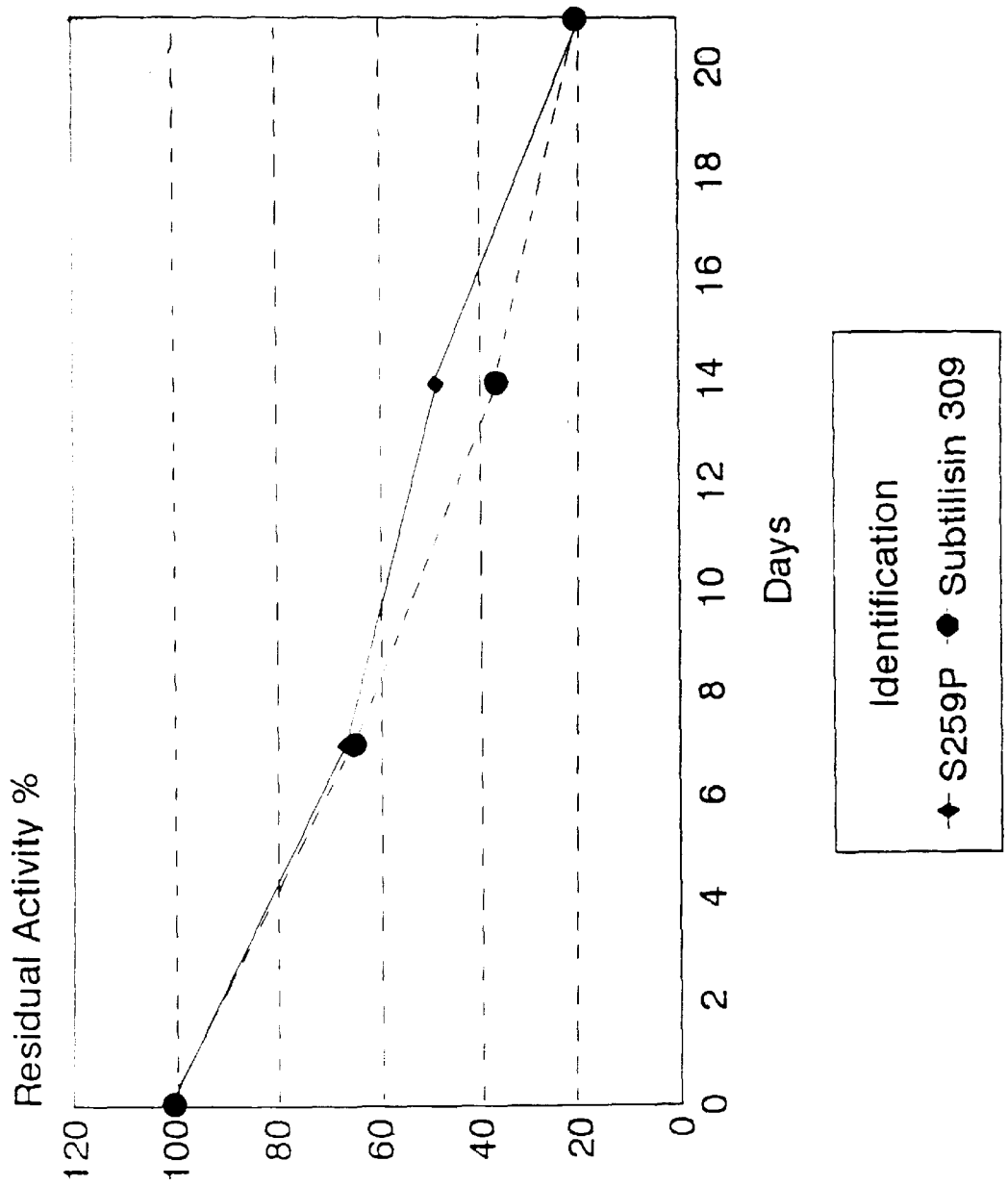
Figure 2C:
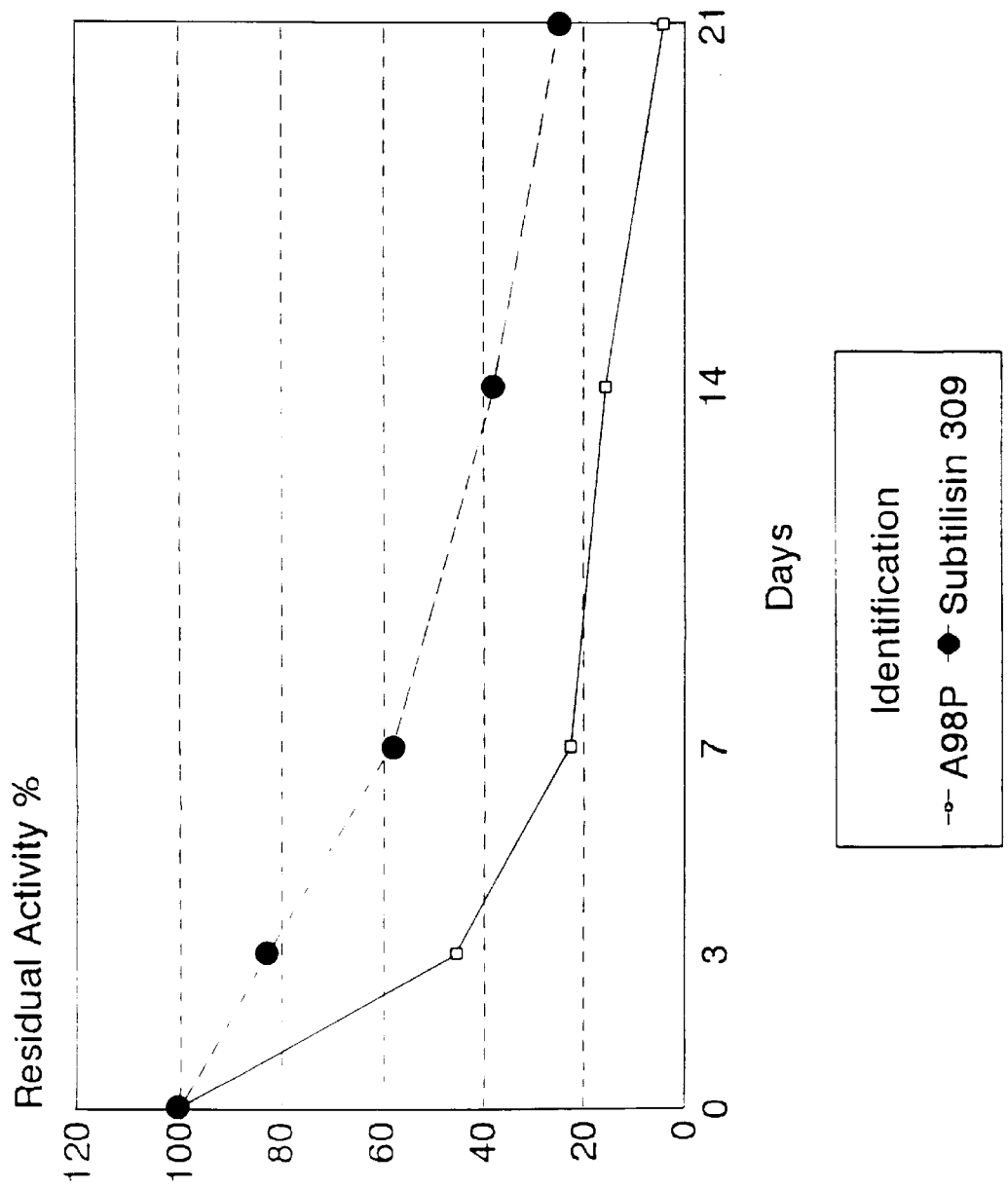
Figure 2D:
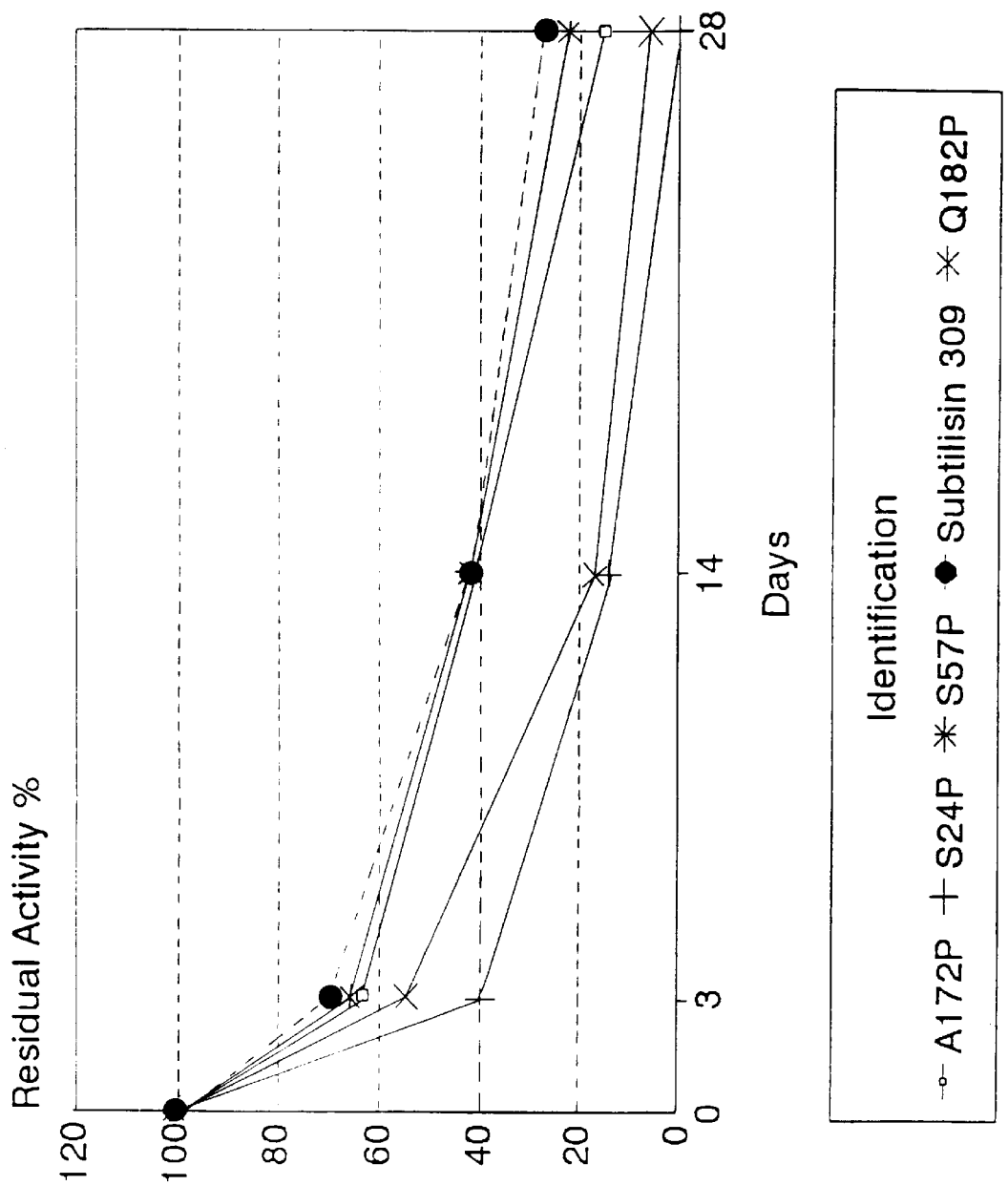
Figure 2E:
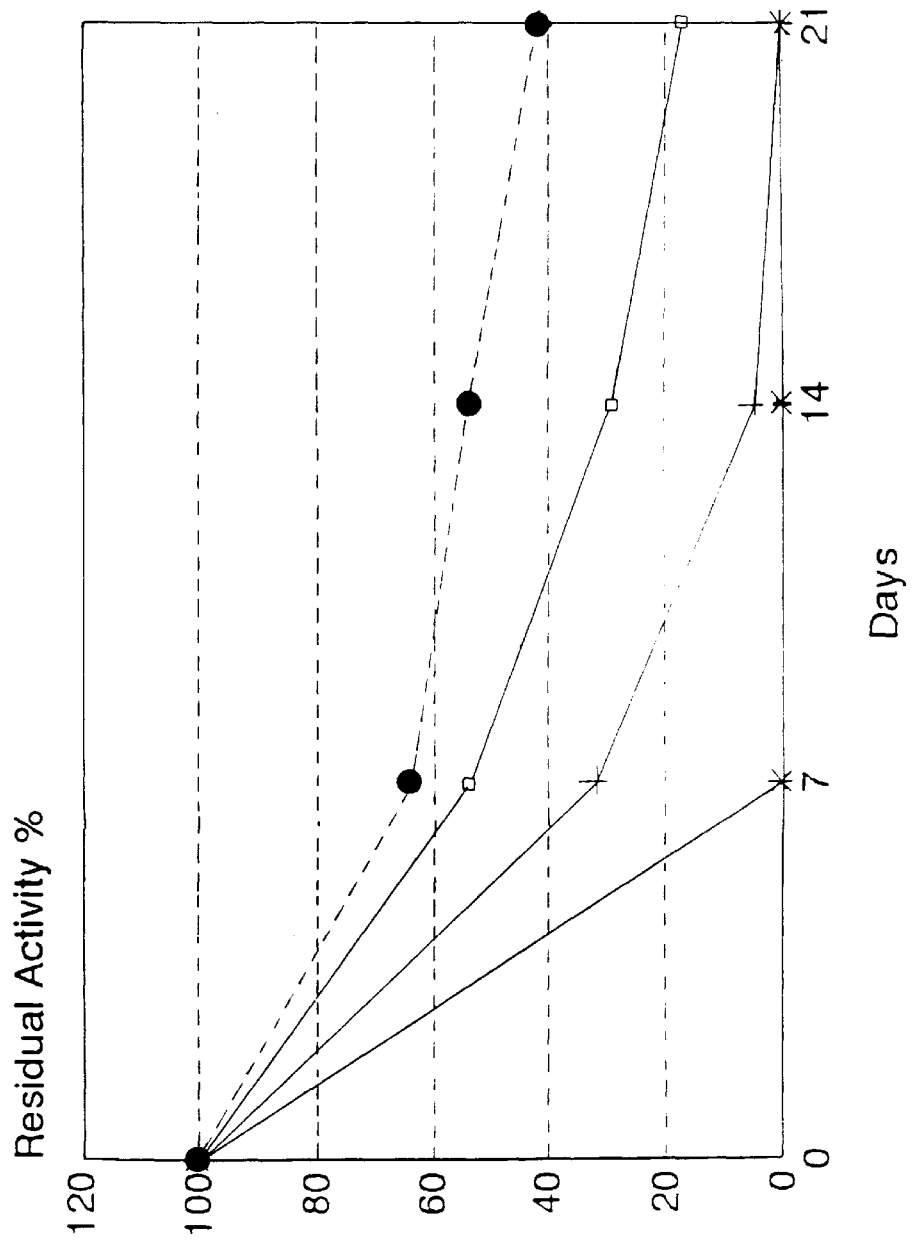

The storage stability generally reflects the thermostability, i.e. improved thermostability corresponds with improved storage stability. The improvement in thermostability of purified variants has been tested by a differential scanning calorimetry (DSC) method, vide Example 3 for experimental data. The result of these tests is shown in Table 3, below. The storage stability has been tested by a Mini Storage Test, vide Example 4 for experimental data, and the results of the storage stability test are shown in FIG. 2.

TABLE 3

Stabilization relative to Subtilisin 309

| Variant | Relative stabilization Δ DSC (°C.) |
|---|---|
| S24P | -2.0°C. |
| T38P | -0.1°C. |
| S57P | 0.7°C. |
| A98P | 0.1°C. |
| S99P | -0.2°C. |
| A172P | 0.1°C. |
| Q182P | -2.5°C. |
| S188P | 1.5°C. |
| A194P | 2.6°C. |
| S242P | 1.4°C. |
| S256P | -2.1°C. |
| S259P | 0.6°C. |

It appears from Table 3 that 3 of the variants constructed possess significantly improved thermostability, 2 of the variants possess only slightly improved thermostability, 4 of the variants possess no significant change in thermostability, and 3 of the variants posses significantly decreased thermostability, when compared to the wild-type enzyme.

These results demonstrate that although a clear rationale exists for stabilization by introduction of proline residues into a protein by the Phi-Psi-Concept described in this specification, no conclusion as to the stabilizing effect of the individual variants is predictable.

However, when a variant with improved thermostability has been obtained, the stabilizing effect of individual mutations in general is considered additive. This is demonstrated in Table 4 below, where the thermal denaturation temperatures, as measured by differential scanning calorimetry (DSC), of Subtilisin 309 variants relative to the wild-type enzyme are presented.

Thus, stabilized protease variants which, further to the stabilizing proline residue(s) inserted, contain one or more additional stabilizing mutations as described in this specification, are considered within the scope of this invention.

TABLE 4

Additive Stabilizing Effect in Subtilisin 309 Variants
Figures in parenthesis indicate the sum of Δ DSC temperatures for variants tested individually.

| Variants | | | | | | | | Δ DSC (°C.) | |
|---|---|---|---|---|---|---|---|---|---|
| G195E | | | | | | | | 0.1 | |
| | H120D | | | | | | | 0.2 | |
| | | K235L | | | | | | 0.0 | |
| | | | *36D | | | | | 4.0 | |
| | | | | N76D | | | | 4.3 | |
| | | | | | A194P | | | 2.6 | |
| | | | | | | G97N | | -0.3 | |
| | | | | | | | V104Y | 2.3 | |
| G195E | H120D | K235L | | | | | | 0.3 | (0.3) |
| G195E | H120D | K235L | *36D | | | | | 4.0 | (4.3) |
| G195E | H120D | K235L | *36D | | A194P | | | 7.0 | (6.9) |
| G195E | H120D | K235L | *36D | N76D | | | | 7.0 | (8.6) |
| G195E | H120D | K235L | *36D | N76D | A194P | | | 10.4 | (11.2) |
| G195E | H120D | | *36D | | A194P | G97N | | 7.4 | (6.6) |
| G195E | H120D | | *36D | | A194P | G97N | V104Y | 8.2 | (8.2) |
| G195E | H120D | K235L | *36D | | A194P | G97N | | 6.9 | (6.6) |
| G195E | H120D | K235L | *36D | | A194P | G97N | V104Y | 8.0 | (8.9) |

Method For Producing Mutations In Genes Encoding Proteases

Many methods for introducing mutations into genes are well known in the art. After a brief discussion of cloning subtilisin genes, methods for generating mutations at specific sites within the subtilisin gene will be discussed.

Cloning A Subtilisin Gene

The gene encoding subtilisin may be cloned from any Gram-positive bacteria or fungus by various methods, well known in the art. First a genomic, and/or cDNA library of DNA must be constructed using chromosomal DNA or messenger RNA from the organism that produces the subtilisin to be studied. Then, if the amino-acid sequence of the subtilisin is known, homologous, oligonucleotide probes may be synthesized, labelled, and used to identify subtilisin-encoding clones from a genomic library of bacterial DNA, or from a fungal cDNA library. Alternatively, a labelled oligonucleotide probe containing sequences homologous to subtilisin from another strain of bacteria or fungus could be used as a probe to identify subtilisin-encoding clones, using hybridization and washing conditions of lower stringency.

Yet another method for identifying subtilisin-producing clones would involve inserting fragments of genomic DNA into an expression vector, such as a plasmid, transforming protease-negative bacteria with the resulting genomic DNA library, and then plating the transformed bacteria onto agar containing a substrate for subtilisin, such as skim-milk. Those bacteria containing subtilisin-bearing plasmid will produce colonies surrounded by a halo of clear agar, due to digestion of the skim-milk by excreted subtilisin.

Generation Of Site Directed Mutations In The Subtilisin Gene

Once the subtilisin gene has been cloned, and desirable sites for mutagenesis identified, the mutations can be introduced using synthetic oligonucleotides. These oligonucleotides contain nucleotide sequences flanking the desired mutation sites, mutant nucleotides are inserted during oligonucleotide synthesis. In a preferred method, a single stranded gap of DNA, bridging the subtilisin gene, is created in a vector bearing the subtilisin gene. Then the synthetic nucleotide, bearing the desired mutation, is annealed to a homologous portion of the single-stranded DNA. The remaining gap is then filled in by DNA polymerase I (Klenow fragment) and the construct is ligated using T4 ligase. A specific example of this method is described [Morinaga et al. (1984); Biotechnology, 2 646–639]. According to Morinaga et al., a fragment within the gene is removed using restriction endonuclease. The vector/gene, now containing a gap, is then denatured and hybridized to a vector/gene which, instead of containing a gap, has been cleaved with another restriction endonuclease at a site outside the area involved in the gap. A single-stranded region of the gene is then available for hybridization with mutated oligonucleotides, the remaining gap is filled in by the Klenow fragment of DNA polymerase I, the insertions are ligated with T4 DNA ligase, and, after one cycle of replication, a double-stranded plasmid bearing the desired mutation is produced. The Morinaga method obviates the additional manipulation of constructing new restriction sites, and, therefore, facilitates the generation of mutations at multiple sites. U.S. Pat. No. 4,760,025, by Estell et al., issued Jul. 26, 1988, is able to introduce oligonucleotides bearing multiple mutations by performing minor alterations of the cassette, however, an even greater variety of mutations can be introduced at any one time by the Morinaga method, because a multitude of oligonucleotides, of various lengths, can be introduced.

Expression Of Subtilisin Variants

According to the invention, a mutated subtilisin gene produced by methods described above, by the method described in Example 1, or any alternative methods known in the art, can be expressed, in enzyme form, using an expression vector. An expression vector generally falls under the definition of a cloning vector, since an expression vector usually includes the components of a typical cloning vector, namely, an element that permits autonomous replication of the vector in a microorganism independent of the genome of the microorganism, and one or more phenotypic markers for selection purposes. An expression vector includes control sequences encoding a promoter, operator, ribosome binding site, translation initiation signal, and, optionally, a repressor gene or various activator genes.

To permit the secretion of the expressed protein, nucleotides encoding a "signal sequence" may be inserted prior to the coding sequence of the gene. For expression under the direction of control sequences, a target gene to be treated according to the invention is operably linked to the control sequences in the proper reading frame. Promoter sequences that can be incorporated into plasmid vectors, and which can support the transcription of the mutant subtilisin gene, include but are not limited to the prokaryotic B-lactamase promoter [Villa-Kamaroff, et al. (1978); Proc. Natl. Acad. Sci. U.S.A.; 75 3727–3731] and the tac promoter [DeBoer, et al. (1983); Proc. Natl. Acad. Sci. U.S.A.; 80 21–25]. Further references can also be found in "Useful proteins from recombinant bacteria" in Scientific American (1980); 242 74–94.

According to one embodiment, *B. subtilis* is transformed by an expression vector carrying the mutated DNA. If expression is to take place in a secreting microorganism such as *B. subtilis* a signal sequence may follow the translation initiation signal and precede the DNA sequence of interest. The signal sequence acts to transport the expression product to the cell wall where it is cleaved from the product upon secretion. The term "control sequences" as defined above is intended to include a signal sequence, when it is present.

The microorganisms able to produce a stabilized enzyme of this invention can be cultivated by conventional fermentation methods in a nutrient medium containing assimilable carbon and nitrogen together with other essential nutrients, the medium being composed in accordance with the principles of the known art.

Nucleotide Sequences And Microorganisms

This invention also relates to DNA nucleotide sequences encoding a stabilized protease of the invention, and to an expression vector containing a DNA nucleotide sequence encoding a stabilized protease.

The stabilized protease may be expressed and produced when DNA nucleotide sequence encoding this protease is inserted into a suitable expression vector in a suitable host organism. The host organism is not necessarily identical to the organism from which the parent gene originated. The construction of the mutated genes, vectors and mutant and transformed microorganisms may be carried out by any appropriate recombinant DNA technique, known in the art.

The invention also relates to host organisms containing an expression vector carrying a DNA nucleotide sequence encoding a stabilized protease.

Detergent Compositions

The present invention also comprises the use of the stabilized proteases of the invention in cleaning and detergent compositions and such composition comprising the stabilized proteases.

Such compositions comprise any one or more of the proteases of the invention alone or in combination with any of the usual components included in such compositions which are well-known to the person skilled in the art.

Such components comprise builders, such as phosphate or zeolite builders, surfactants, such as anionic, cationic, non-ionic or zwitterionic type surfactants, polymers, such as acrylic or equivalent polymers, bleach systems, such as perborate- or amino-containing bleach precursors or activators, structurants, such as silicate structurants, alkali or acid to adjust pH, humectants, and/or neutral inorganic salts.

The detergent compositions of the invention can be formulated in any convenient form such as powders, liquids, etc.

The enzymes can be used in well-known standard amounts in detergent compositions. The amounts may range very widely, e.g. about 0.0002–0.01, e.g. about 0.005–0.05, Anson units per gram of the detergent composition. Expressed in alternative units, the protease can be included in the compositions in amounts in the order of from about 0.1 to 100 GU/mg (e.g. 1–50, especially 5–20 GU/mg) of the detergent formulation, or any amount in a wide range centering at about 0.01–4, e.g. 0.1–0.4 KNPU per g of detergent formulation.

The KNPU has been defined previously. A GU is a Glycine Unit, defined as the proteolytic enzyme activity which, under standard conditions, during a 15-minutes' incubation at 40 deg C., with N-acetyl casein as substrate, produces an amount of $NH_2$-group equivalent to 1 micromole of glycine.

It may for example be suitable to use the present enzymes at the rate of about 0.25 mg of enzyme protein per liter of wash liquor, corresponding to an enzyme activity of the order of 0.08 KNPU per liter. Corresponding detergent formulations can contain the enzymes in for example an amount of the order of 0.1–0.4 KNPU/g.

The detergent compositions may also contain further enzymes.

For example, lipase can usefully be added in the form of a granular composition (alternatively a solution or a slurry) of lipolytic enzyme with carrier material (e.g. as in EP Patent Publication No. 258,068 (Novo Nordisk ANS) and the Lipolase™ and other enzyme compositions of Novo Nordisk A/S).

The added amount of lipase can be chosen within wide limits, for example 50 to 30,000 LU/g per gram of the surfactant system or of the detergent composition, e.g. often at least 100 LU/g, very usefully at least 500 LU/g, sometimes preferably above 1000, above 2000 LU/g or above 4000 LU/g or more, thus very often within the range of 50–4000 LU/g, and possibly within the range of 200–1000 LU/g. In this specification, lipase units are defined as they are in EP Patent Publication No. 258,068.

The lipolytic enzyme can be chosen among a wide range of lipases. In particular, the lipases described in for example the following patent specifications: EP Patent Publications Nos. 214,761 (Novo Nordisk A/S), 258,068, and especially lipases showing immunological crossreactivity with antisera raised against lipase from Thermomyces lanuginosus ATCC 22070, EP Patent Publications Nos. 205,208 and 206,390, and especially lipases showing immunological cross-reactivity with antisera raised against lipase from Chromobacter viscosum var lipolyticum NRRL B-3673, or against lipase from Alcaligenes PL-679, ATCC 31371 and FERM-P 3783, also the lipases described in specifications WO 87/00859 (Gist-Brocades) and EP Patent Publication No. 204,284 (Sapporo Breweries). Suitable, in particular, are for example the following commercially available lipase preparations: Lipolase Novo Nordisk ANS, Amano lipases CE, P, B, AP, M-AP, AML, and CES, and Meito lipases MY-30, OF, and PL, also Esterase MM, Lipozym, SP225, SP285, Saiken lipase, Enzeco lipase, Toyo Jozo lipase and Diosynth lipase (Trade Marks).

Amylase can for example be used when desired, in an amount in the range of about 1 to about 100 MU (maltose units) per gram of detergent composition (or 0.014–1.4, e.g. 0.07–0.7, KNU/g (Novo units)). Cellulase can for example be used when desired, in an amount in the range of about 0.3 to about 35 CEVU units per gram of the detergent composition.

Among the usual detergent ingredients which may be present in usual amounts in the detergent compositions of this invention are the following: The compositions may be built or unbuilt, and may be of the zero-P type (i.e. not containing any phosphorus containing builders). Thus, the composition may contain in the aggregate for example from 1–50%, e.g. at least about 5% and often up to about 35–40% by weight, of one or more organic and/or inorganic builders. Typical examples of builders include those already mentioned above, and more broadly include alkali metal ortho, pyro, and tripolyphosphates, alkali metal carbonates, either alone or in admixture with calcite, alkali metal citrates, alkali metal nitrilotriacetates, carboxymethyloxysuccinates, zeolites, polyacetalcarboxylates, and so on.

Furthermore, the detergent compositions may contain from 1–35% of a bleaching agent or a bleach precursor or a system comprising bleaching agent and/or precursor with activator therefor. Further optional ingredients are lather boosters, foam depressors, anti-corrosion agents, soil-suspending agents, sequestering agents, anti-soil redeposition agents, perfumes, dyes, stabilising agents for the enzymes, and so on.

The compositions can be used for the washing of textile materials, especially, but without limitation cotton and polyesterbased textiles and mixtures thereof. For example washing processes carried out at temperatures of about 60°–65° C. or lower, e.g. about 30°–35° C. or lower, are particularly suitable. It can be very suitable to use the compositions at a rate sufficient to provide about e.g. 0.4–0.8 g/l of surfactant in the wash liquor, although it is of course possible to use lower or higher concentrations, if desired. Without limitation it can for example be stated that a use-rate from about 1 to 10 g/l, e.g. from about 3–6 g/l, of the detergent formulation is suitable for use in the case when the formulations are substantially as in the Examples.

In some useful embodiments, the detergent compositions can be formulated as follows:

Detergent I

A detergent powder according to an embodiment of the invention containing zeolite builder is formulated to contain:

Total active detergent of about 16%, anionic detergent of about 9%, nonionic detergent of about 6%, zeolite-containing builder of about 20%, acrylic or equivalent polymer of about 3.5%, perborate bleach precursor of about 6–18%, amino-containing bleach activator of about 2%, silicate or other structurant of about 3.5%, alternatively down to about 2.5%, enzyme of about 8 (alternatively of about 15) glycine units/mg grade, with alkali to adjust to desired pH in use, and neutral inorganic salt, and enzymes (about 0.5% each enzyme).

The anionic detergent is a mixture of sodium dodecylbenzene sulphonate, alternatively sodium linear alkylbenzene-sulphonate, 6% and primary alkyl sulphate of 3%. The nonionic detergent is an ethoxylate of an approx. C13–C15 primary alcohol with 7 ethoxylate residues per mole. The zeolite builder is type A zeolite. The polymer is polyacrylic acid. The perborate bleach precursor is sodium tetraborate tetrahydrate or monohydrate. The activator is tetraacetyl-ethylenediamine. The structurant is sodium silicate. The neutral inorganic salt is sodium sulphate.

Detergent II

An aqueous detergent liquid according to an embodiment of the invention is formulated to contain:

Dodecylbenzene-sulphonic acid of 16%, C12–C15 linear alcohol condensed with 7 mol/mol ethylene oxide of 7%, monoethanolamine of 2%, citric acid of 6.5%, sodium xylenesulphonate of 6%, sodium hydroxide of about 4.1%, protease of 0.5%, minors and water to 100%. The pH is adjusted to a value between 9 and 10.

In other useful embodiments, the detergent compositions can be formulated as e.g. in International Patent Publications Nos. WO 91/00334, WO 91/00335, and International Patent Application No. PCT/DK91/00399.

The invention is further illustrated in the following examples, which are not intended to be in any way limiting to the scope of the invention as claimed.

EXAMPLE 1

Preparation Example

In the following Example, showing a presently preferred method for constructing and expressing genes to code for wild-type and variant protease enzymes in accordance with embodiments of the present invention, the following materials are referred to:

*B. subtilis* 309 and 147 are variants of *Bacillus lentus*, deposited with the NCIB and accorded the accession numbers NCIB 10147 and NCIB 10309, and described in U.S. Pat. No. 3,723,250 incorporated by reference herein.

*E. coli* MC 1000 (M. J. Casadaban and S. N. Cohen (1980); J. Mol. Biol.; 138 179–207), was made r–,m+ by conventional methods and is also described in U.S. patent application Ser. No. 039,298.

A vector suited to a synthetic gene coding for subtilisin 309 and its mutants was constructed. It is essentially a pUC19 plasmid [C. Yanish-Perron and J. Messing (1985); Gene; 33 103–119], in which the multiple cloning site has been replaced by a linker containing the restriction sites used to separate the five subfragments constituting the gene. The new linker was inserted into Eco RI—HindIll cut pUC19 thereby destroying these sites.

oligonucleotides have been phosphorylated. Duplexes (indicated in sheets 1/7 to 4/7) were formed from corresponding pairs of oligonucleotides by heating for 5 min at 90 deg C. followed by cooling to room temperature over a period of 75 min. The duplexes were mixed and treated with T4 DNA ligase.

The five subfragments were isolated on a 2% agarose gel and inserted into pSX191. The sequence was verified by dideoxynucleotide sequencing. Fragments A–E were isolated and ligated together with KpnI-BamHI cut pSX191. The ligation mixtures were used to transform competent *E coli* MC1000 r–,m+ selecting for ampicillin resistance. The 850 bp KpnI-BamHI fragment that constitutes the part of the subtilisin 309 gene coding for the mature part of the enzyme was then used to replace the wild type gene on pSX212 giving rise to pSX222, which was then transformed into competent B subtilis SHa273. After fermentation of the transformed strain and purification of the enzyme it was shown that the product was indistinguishable from the wild type product.

Protease variants derived from the synthetic gene are made by using oligonucleotides with altered sequence at the place(s) where mutation is wanted (e.g. with sequences as given below) and mixing them with the rest of the oligonucleotides appropriate to the synthetic gene. Assembly of the variant gene is carried out with the variant materials in a manner otherwise analogous to that described above. Further information on synthetic genes generally is available in Agarval et al (1970); Nature; 227 27–34.

Figure 1H:
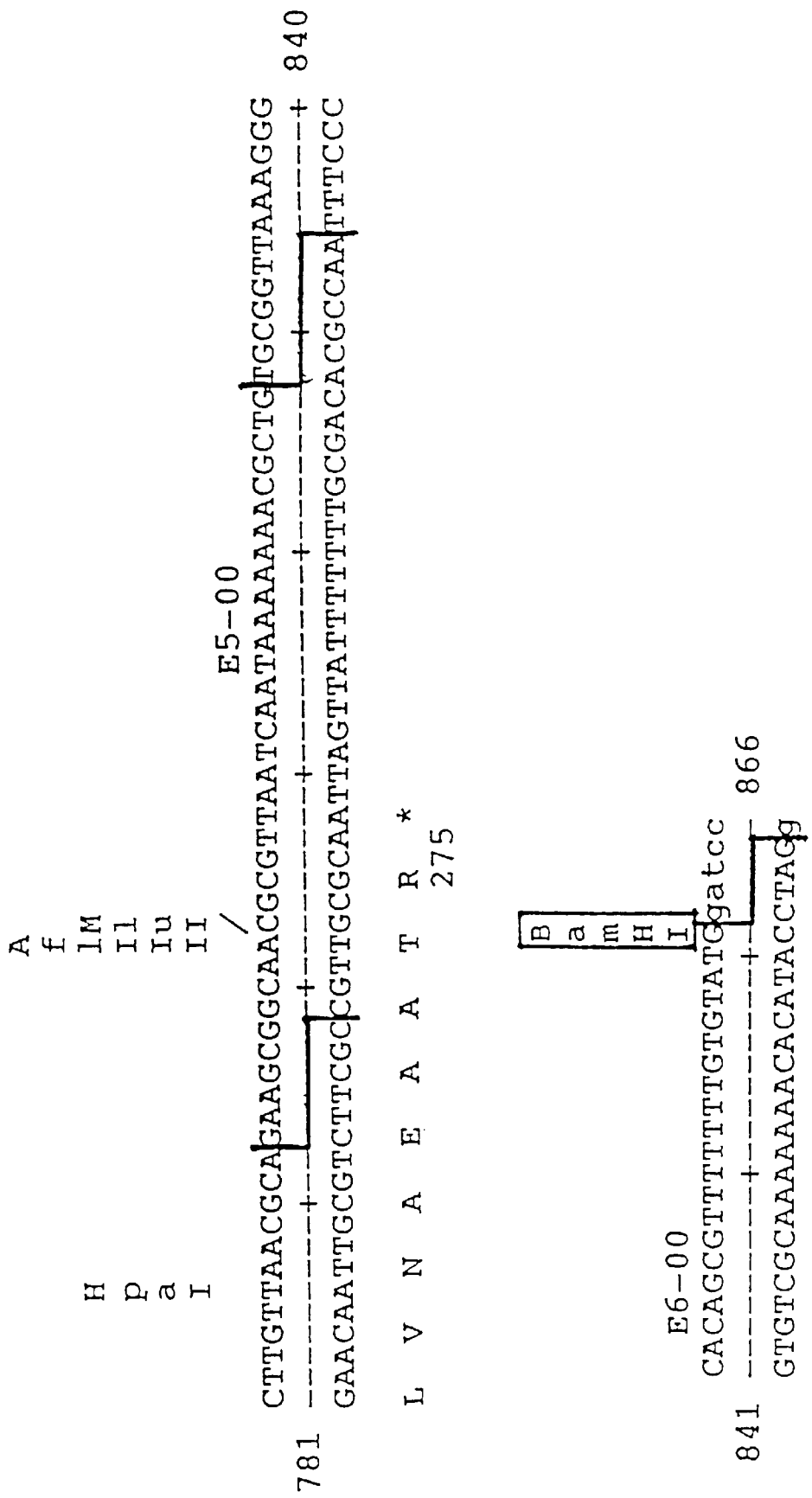
Figure 1K:
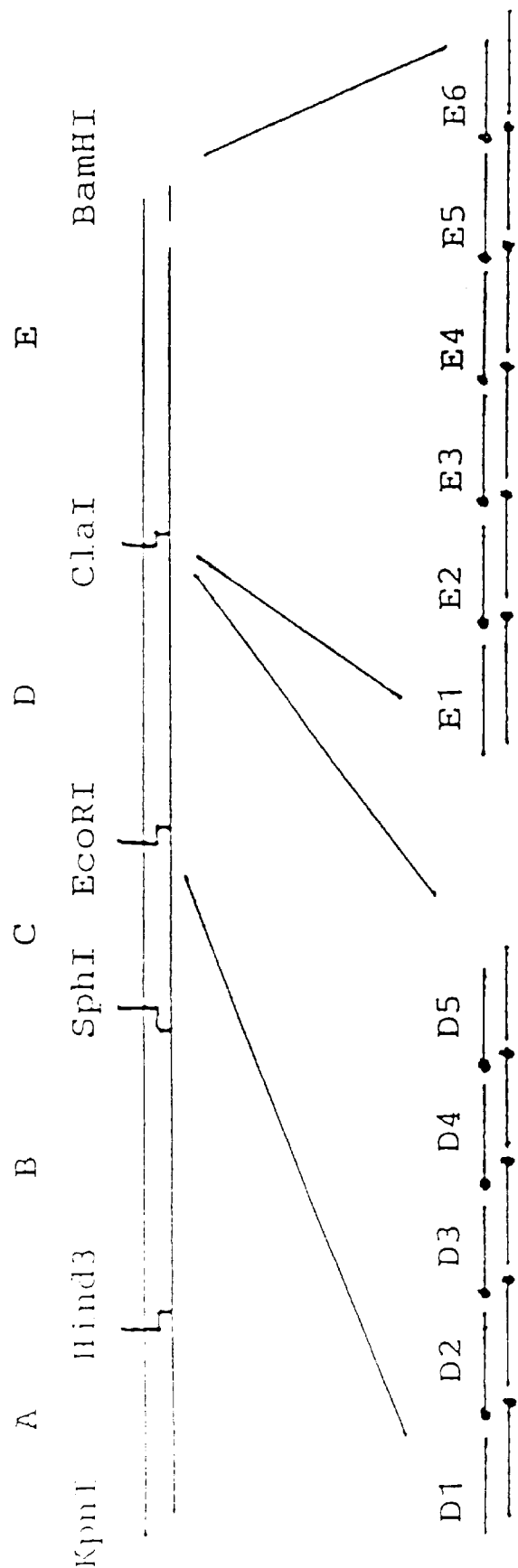
Figure 1L:
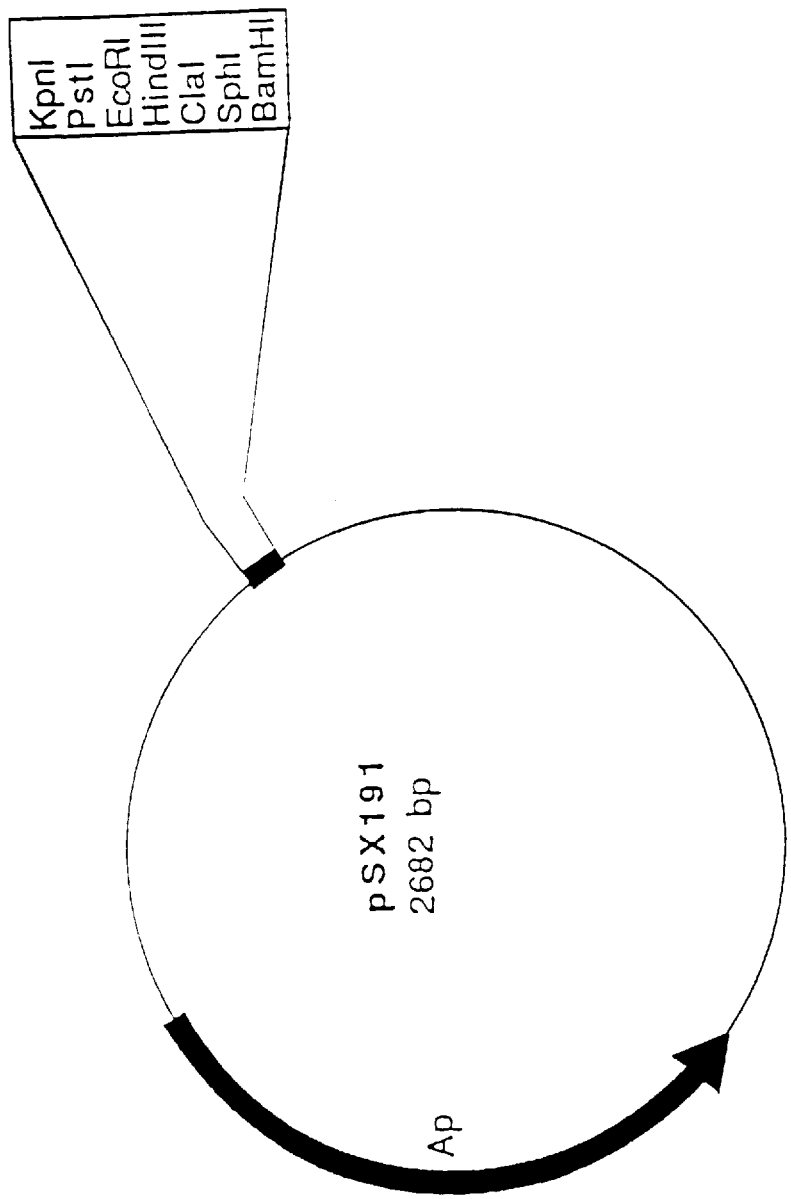
Figure 1N:
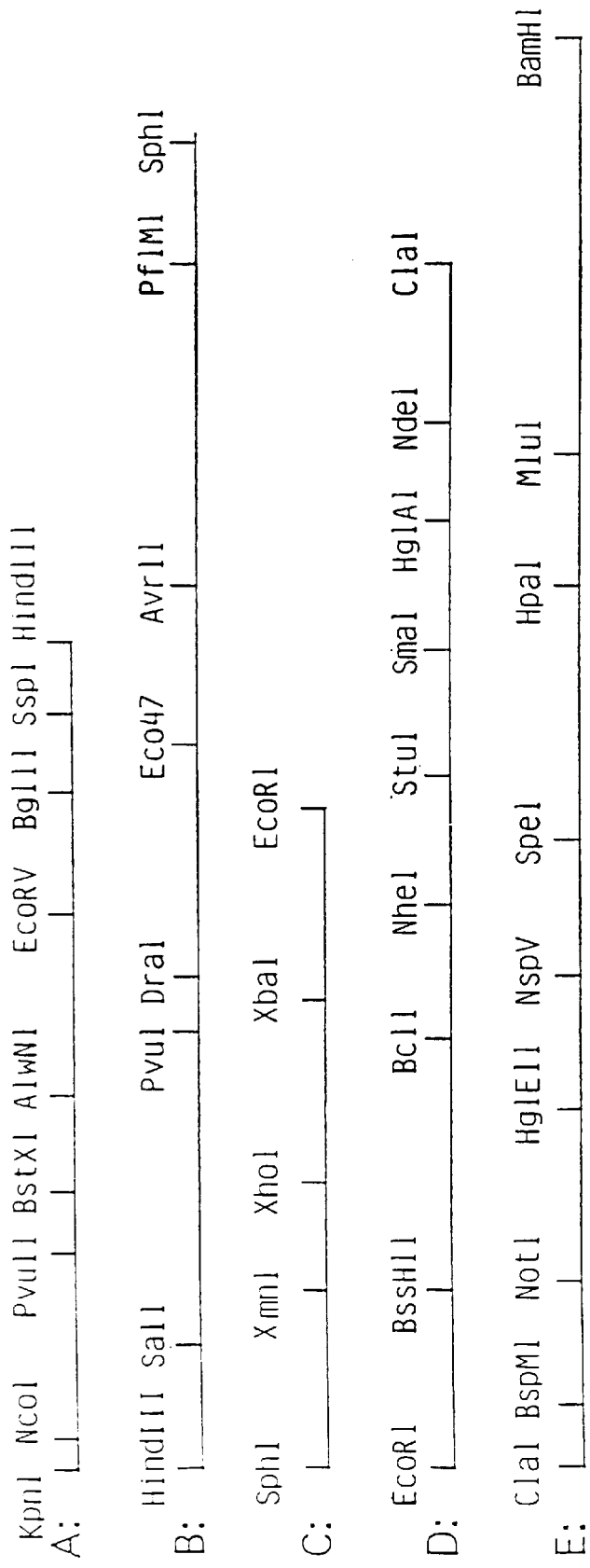
Figure 10:
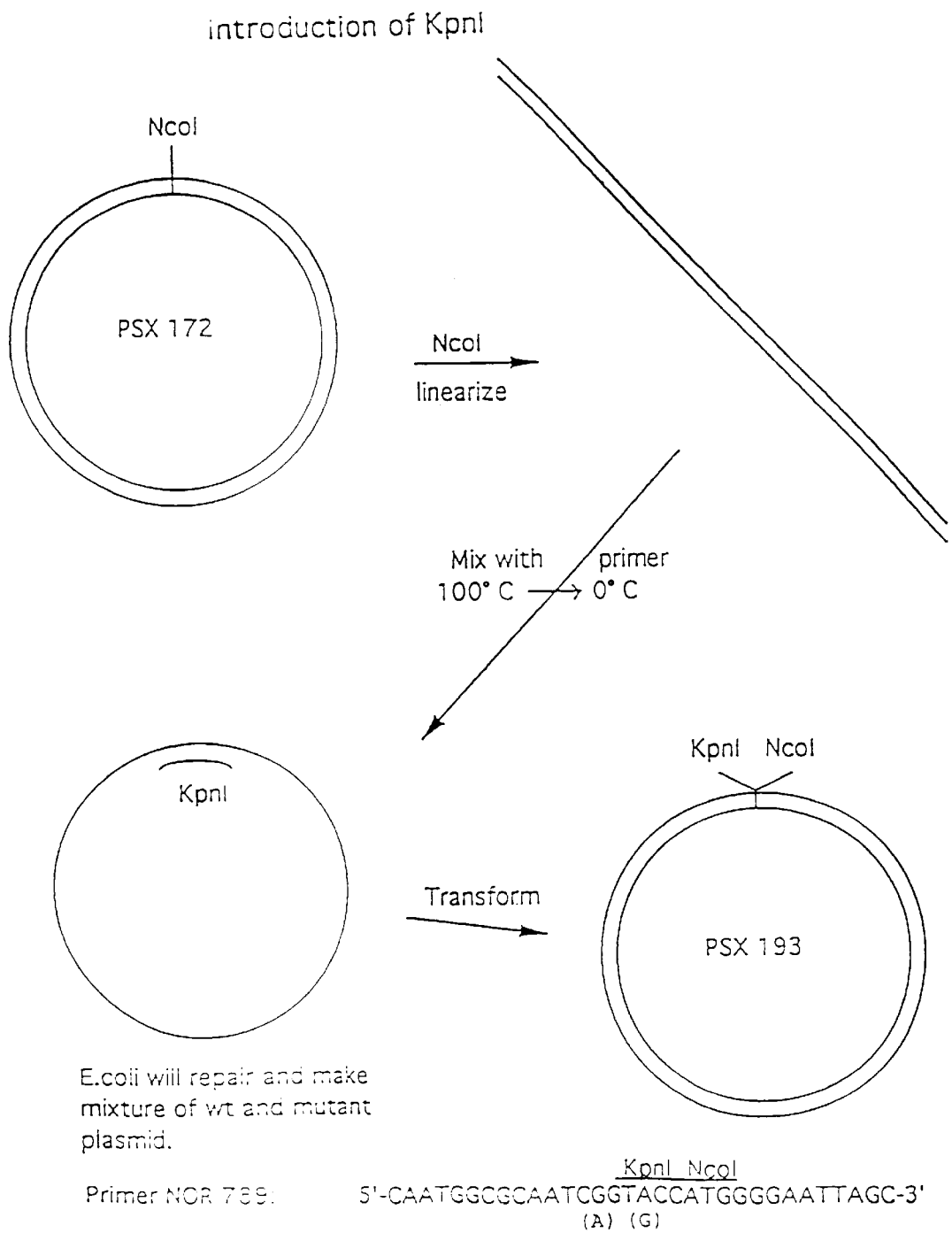

A KpnI site was introduced into the beginning of the subtilisin 309 synthetic gene encoding the mature part of the enzyme. The method used is called oligonucleotide directed double-strand break repair mutagenesis and is described by Wlodek Mandecki (1986); Proc. Nat. Acad. Sci. USA; 83 7177–7181. pSX1 72 is opened with NcoI at the beginning of the mature part of the subtilisin 309 gene and is mixed with the oligonucleotide NOR 789 (sequence shown in FIG. 1 (7/7)), heated to 100 deg C., cooled to 0 deg C., and transformed into *E coli*. After retransformation, the recombinants can be screened by colony hybridisation using 32-P-labelled NOR 789. The recombinants that turned out to be positive during the screening had the KpnI site introduced right in front of NcoI by changing two bases without changing the amino acid sequence. pSX172 is described in EP Patent Publication No. 405,901. The KpnI site so created is inserted into pSX120 on a 400-bp PvuI-NheI fragment,

```
   (RI) KpnI  PstI   EcoRI   Hind3  ClaI      SphI   Bam   (H3)
5'-AATTGGTACCCTGCAGGAATTCAAGCTTATCGATGGCATGCGGATCC-3'(SEQ ID NO:1)
   3'-CCATGGGACGTCCTTAAGTTCGAATAGCTACCGTACGCCTAGGTCGA-5'(SEQ ID NO:2)
```

A synthetic gene coding for the mature part of subtilisin 309 was constructed as shown by the following description and the diagrams given in FIG. 1 (sheets 1/7 to 7/7) of the accompanying drawings. The structure of the synthetic gene is summarised in sheets 1/7 to 4/7, which also indicate fragments used in the construction. Each subfragment was made from 6 to 12 oligonucleotides. The oligonucleotides were synthesised on an automatic DNA synthesizer using phosphoramidite chemistry on a controlled glass support [S. L. Beaucage and M. H. Carruthers (1981); Tetrahedron Letters; 22 1859–1869]. Dots in the 5'-end of the oligonucleotides in the Figures are meant to indicate that these giving rise to pSX212. pSX120 is also described in EP Patent Publication No. 405,901.

The synthetic gene is inserted between KpnI and BamHI on pSX212, giving rise to pSX222.

Examples of mutations and corresponding sequences of oligonucleotides are as follows:

A194P (fragmnet D3)
5'-AACAACCGCGCTAGCTTTTCACAGTATGGCCCAGGC-3'(SEQ ID NO:3)
   ||||||||||||||||||||||||||*|||||
       3'-GCGCGATCGAAAAGTGTCATACCGGGTCCGGAACTG-5'(SEQ ID NO:4)

A172P (fragment D2)
5'-CGCTATCCGAACGCAATGGCAGTCGGAGCTACTGATCAAAAC-3'(SEQ ID NO:5)
   *|||||||||||||||||||||||||||||||||||||||
       3'-GGCTTGCGTTACCGTCAGCCTCGATGACTAGTTTTGTTGTTG-5'(SEQ ID NO:6)

S57P (fragment B1)
5'-AGCTTTGTACCAGGGGAACCGCCGACTCAAGATGGG-3'(SEQ ID NO:7)
   ||||||||||||||||*|||||||||||||||
       3'-AACATGGTCCCCTTGGCGGCTGAGTTCTACCCTTACCC-5'(SEQ ID NO:8)

These oligonucleotides were combined with the rest of the oligonucleotides from the synthetic gene that was not changed.

EXAMPLE 2

Purification Example

This procedure relates to purification of a 10 liter scale fermentation of the Subtilisin 147 enzyme, the Subtilisin 309 enzyme or mutants thereof.

Approximately 8 liters of fermentation broth were centrifuged at 5000 rpm for 35 minutes in 1 liter beakers. The supernatants were adjusted to pH 6.5 using 10% acetic acid and filtered on Seitz Supra S100 filter plates.

The filtrates were concentrated to approximately 400 ml using an Amicon CH2A UF unit equipped with an Amicon S1Y10 UF cartridge. The UF concentrate was centrifuged and filtered prior to absorption at room temperature on a Bacitracin affinity column at pH 7. The protease was eluted from the Bacitracin column at room temperature using 25% 2-propanol and 1M sodium chloride in a buffer solution with 0.01 dimethylglutaric acid, 0.1M boric acid and 0.002M calcium chloride adjusted to pH 7.

The fractions with protease activity from the Bacitracin purification step were combined and applied to a 750 ml Sephadex G25 column (5 cm dia.) equilibrated with a buffer containing 0.01 dimethylglutaric acid, 0.2M boric acid and 0.002 m calcium chloride adjusted to pH 6.5.

Fractions with proteolytic activity from the Sephadex G25 column were combined and applied to a 150 ml CM Sepharose CL 6B cation exchange column (5 cm dia.) equilibrated with a buffer containing 0.01M dimethylglutaric acid, 0.2M boric acid, and 0.002M calcium chloride adjusted to pH 6.5.

The protease was eluted using a linear gradient of 0–0.1M sodium chloride in 2 liters of the same buffer (0–0.2M sodium chloride in case of sub 147).

In a final purification step protease containing fractions from the CM Sepharose column were combined and concentrated in an Amicon ultrafiltration cell equipped with a GR81PP membrane (from the Danish Sugar Factories Inc.).

EXAMPLE 3

Differential Scanning Calorimetry

The purified protease variants were subjected to thermal analysis by Differential Scanning Calorimetry (DSC).

The instrument was a Setaram micro DSC apparatus connected to HP86 computer for data collection and analysis. Setaram software was used.

The enzyme was diluted to a concentration of preferably 2 mg/ml in a liquid built detergent (pH 8.5) of the following composition:

| | |
|---|---|
| AE[1] ($C_{12-14}$); EO 6 | 15% |
| LAS[2] ($C_{12}$) | 10% |
| Coconut fatty acid | 9% |
| Oleic acid ($C_{18}$) | 1% |
| Triethanolamin (pKA 7.9) | 9% |
| Glycerol | 10.5% |
| Ethanol | 1.5% |
| Sodium citrate | 8% |
| CaCl; $2H_2O$ | 0.1% |
| NaOH | 1% |
| Water | 34.9% |

[1]Alcohol ethoxylate
[2]Linear alkylbenzene sulphonate

The heating rate was 0.5° C./min from 25° C. to 90° C.

The stabilization of Subtilisin 309 variants relative to wild type enzyme measured by this method is presented in Table 3, above.

EXAMPLE 4

Storage Stability

The storage stability of the enzymes of the invention was determined and compared to the storage stability of subtilisin 309 (wild-type). This stability test is performed as a Mini Storage Test. In each tube 100 µl of sample were used.

The enzyme dosages were 0.25 mg enzyme/g detergent. A liquid detergent composition was used in this test, vide Detergent II, supra.

The tubes were incubated at 35° C. for 3, 7, 14, and 21 days, respectively, and the residual activity determined.

The residual activity determination method was based on the digestion of a dimethyl casein (DMC) solution by the proteolytic enzymes. The primary amino groups formed in this process react with trinitrobenzene sulphonic acid (TNBS) forming a coloured complex. The reaction is followed in situ in order that the change in absorbance per time unit can be calculated.

Since the detergent might contain compounds with primary amino groups, it is necessary to examine this and make correction of the detergent effect. Correction is made by measuring the blind value of the pure detergent and subtracting this value from the value measured as described above.

The activity is determined relative to a sample which immediately after preparation is frozen and kept at a temperature of −10° C. until analysis. The activity of this sample is set to 100%. The activity of the corresponding samples from the storage test is determined relative to the 100% sample.

The reaction conditions were:

| | |
|---|---|
| Temperature: | 40° C. |
| pH: | 8.3 |
| Wavelength: | 420 nm |
| Reaction time: | 9 min. |
| Measuring time: | 3 min. |
| Apparatus: | <COBAS> FARA II centrifugal analyzer from Roche. |

All activities were determined in duplicate.

A folder, AF 285/1 (or later editions), describing this analytical method is available upon request to Novo Nordisk A/S, Denmark, which folder is hereby included by reference.

The result of the storage stability test is shown in FIG. 2. In general, thermostability as determined by DSC and storage stability correlate well.

EXAMPLE 5

Wash Performance

The wash performance tests were accomplished on grass juice soiled cotton in a model wash at 20° C., isothermically for 10 minutes.

As detergent 5 g/l of a powder detergent was used, vide Detergent I, supra. pH was adjusted by addition of NaOH/HCl to 10.2. The water used was approximately 9° dH (German Hardness) for the tests presented in Table 5. For the tests presented in Table 6, 6° dH water was used. The textile/wash liquor ratio was 6 g textile per liter of wash liquor.

Tests were performed at enzyme concentrations of: 0, 0.025, 0.05, 0.1, 0.5, 1.0, and 2.0 mg enzyme protein/l. Two independent sets of tests were performed for each of the enzymes. The results shown in Tables 5–6 are means of these tests.

Subsequent to washing, the fabric was rinsed in running tap water and air-dried. The protease performance was determined by the change ($\Delta R$) of the remission (% R) at 460 nm measured on a Datacolor Elrephometer 2000, $\Delta R$ being the remission after wash with protease added minus the remission after wash with no protease added.

Results from the wash performance tests are presented in Tables 5–6. It is found that all the variants, except Subtilisin 309/S256P, perform at least equal to subtilisin 309 (wild-type).

TABLE 5

Differential Remission, delta R

| | Enzyme dosage mg enzyme/l detergent | | | | | |
|---|---|---|---|---|---|---|
| Variant | 0.025 | 0.05 | 0.1 | 0.5 | 1.0 | 2.0 |
| S57P | 2.4 | 4.4 | 7.4 | 16.8 | 20.0 | 22.1 |
| A172P | 2.4 | 4.4 | 7.5 | 16.9 | 20.1 | 22.3 |
| S188P | 2.2 | 4.8 | 7.5 | 16.9 | 20.9 | 21.7 |
| A194P | 2.5 | 5.3 | 7.6 | 17.5 | 20.5 | 20.8 |
| Subt. 309 | 3.2 | 4.6 | 6.9 | 16.1 | 20.4 | 20.7 |
| S259P | 1.7 | 2.5 | 3.9 | 6.7 | 7.2 | 7.0 |
| Subt. 309 | 0.8 | 2.2 | 3.6 | 5.8 | 6.5 | 6.6 |

TABLE 6

Differential Remission, delta R

| | Enzyme dosage mg enzyme/l detergent | | | | | |
|---|---|---|---|---|---|---|
| Variant | 0.025 | 0.05 | 0.1 | 0.5 | 1.0 | 2.0 |
| T38P | 1.9 | 3.7 | 7.0 | 14.7 | 16.9 | 16.7 |
| S99P | 1.8 | 3.1 | 5.4 | 15.4 | 16.4 | 16.9 |
| S256P | 0.7 | 1.5 | 3.0 | 9.7 | 15.2 | 16.8 |
| Subt. 309 | 1.9 | 3.9 | 6.9 | 14.5 | 16.2 | 17.1 |

---

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

AATTGGTACC CTGCAGGAAT TCAAGCTTAT CGATGGCATG CGGATCC      47

( 2 ) INFORMATION FOR SEQ ID NO:2:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( i i ) MOLECULE TYPE: DNA (genomic)

(x i) SEQUENCE DESCRIPTION: SEQ ID NO:2:

AGCTGGATCC GCATGCCATC GATAAGCTTG AATTCCTGCA GGGTACC    47

(2) INFORMATION FOR SEQ ID NO:3:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (i i) MOLECULE TYPE: DNA (genomic)

(x i) SEQUENCE DESCRIPTION: SEQ ID NO:3:

AACAACCGCG CTAGCTTTTC ACAGTATGGC CCAGGC    36

(2) INFORMATION FOR SEQ ID NO:4:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (i i) MOLECULE TYPE: DNA (genomic)

(x i) SEQUENCE DESCRIPTION: SEQ ID NO:4:

GTCAAGGCCT GGGCCATACT GTGAAAAGCT AGCGCG    36

(2) INFORMATION FOR SEQ ID NO:5:

(i) SEQUENCE CHARACTERISTICS:
    (A) LENGTH: 42 base pairs
    (B) TYPE: nucleic acid
    (C) STRANDEDNESS: single
    (D) TOPOLOGY: linear (i i) MOLECULE TYPE: DNA (genomic)

(x i) SEQUENCE DESCRIPTION: SEQ ID NO:5:

CGCTATCCGA ACGCAATGGC AGTCGGAGCT ACTGATCAAA AC    42

(2) INFORMATION FOR SEQ ID NO:6:

(i) SEQUENCE CHARACTERISTICS:
    (A) LENGTH: 42 base pairs
    (B) TYPE: nucleic acid
    (C) STRANDEDNESS: single
    (D) TOPOLOGY: linear (i i) MOLECULE TYPE: DNA (genomic)

(x i) SEQUENCE DESCRIPTION: SEQ ID NO:6:

GTTGTTGTTT TGATCAGTAG CTCCGACTGC CATTGCGTTC GG    42

(2) INFORMATION FOR SEQ ID NO:7:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (i i) MOLECULE TYPE: DNA (genomic)

(x i) SEQUENCE DESCRIPTION: SEQ ID NO:7:

AGCTTTGTAC CAGGGGAACC GCCGACTCAA GATGGG    36

(2) INFORMATION FOR SEQ ID NO:8:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

```
CCCATTCCCA TCTTGAGTCG GCGGTTCCCC TGGTACAA                                        38
```

(2) INFORMATION FOR SEQ ID NO:9:

(i) SEQUENCE CHARACTERISTICS:
        (A) LENGTH: 275 amino acids
        (B) TYPE: amino acid
        (C) STRANDEDNESS: single
        (D) TOPOLOGY: linear (xi) SEQUENCE DESCRIPTION: SEQ ID NO:9:

```
Ala Gln Ser Val Pro Tyr Gly Val Ser Gln Ile Lys Ala Pro Ala Leu
 1               5                  10                  15
His Ser Gln Gly Tyr Thr Gly Ser Asn Val Lys Val Ala Val Ile Asp
                20                  25                  30
Ser Gly Ile Asp Ser Ser His Pro Asp Leu Lys Val Ala Gly Gly Ala
                35                  40                  45
Ser Met Val Pro Ser Glu Thr Asn Pro Phe Gln Asp Asn Asn Ser His
         50                  55                  60
Gly Thr His Val Ala Gly Thr Val Ala Ala Leu Asn Asn Ser Ile Gly
 65                  70                  75                  80
Val Leu Gly Val Ala Pro Ser Ala Ser Leu Tyr Ala Val Lys Val Leu
                    85                  90                  95
Gly Ala Asp Gly Ser Gly Gln Tyr Ser Trp Ile Ile Asn Gly Ile Glu
               100                 105                 110
Trp Ala Ile Ala Asn Asn Met Asp Val Ile Asn Met Ser Leu Gly Gly
           115                 120                 125
Pro Ser Gly Ser Ala Ala Leu Lys Ala Ala Val Asp Lys Ala Val Ala
    130                 135                 140
Ser Gly Val Val Val Val Ala Ala Ala Gly Asn Glu Gly Thr Ser Gly
145                 150                 155                 160
Ser Ser Ser Thr Val Gly Tyr Pro Gly Lys Tyr Pro Ser Val Ile Ala
                165                 170                 175
Val Gly Ala Val Asp Ser Ser Asn Gln Arg Ala Ser Phe Ser Ser Val
                180                 185                 190
Gly Pro Glu Leu Asp Val Met Ala Pro Gly Val Ser Ile Gln Ser Thr
            195                 200                 205
Leu Pro Gly Asn Lys Tyr Gly Ala Tyr Asn Gly Thr Ser Met Ala Ser
    210                 215                 220
Pro His Val Ala Gly Ala Ala Ala Leu Ile Leu Ser Lys His Pro Asn
225                 230                 235                 240
Trp Thr Asn Thr Gln Val Arg Ser Ser Leu Glu Asn Thr Thr Thr Lys
                245                 250                 255
Leu Gly Asp Ser Phe Tyr Tyr Gly Lys Gly Leu Ile Asn Val Gln Ala
                260                 265                 270
Ala Ala Gln
        275
```

(2) INFORMATION FOR SEQ ID NO:10:

(i) SEQUENCE CHARACTERISTICS:
(A) LENGTH: 269 amino acids
(B) TYPE: amino acid
(C) STRANDEDNESS: single
(D) TOPOLOGY: linear (xi) SEQUENCE DESCRIPTION: SEQ ID NO:10:

| Ala | Gln | Ser | Val | Pro | Trp | Gly | Ile | Ser | Arg | Val | Gln | Ala | Pro | Ala | Ala |
|---|---|---|---|---|---|---|---|---|---|---|---|---|---|---|---|
| 1 | | | | 5 | | | | | 10 | | | | | 15 | |
| His | Asn | Arg | Gly | Leu | Thr | Gly | Ser | Gly | Val | Lys | Val | Ala | Val | Leu | Asp |
| | | | 20 | | | | | 25 | | | | | 30 | | |
| Thr | Gly | Ile | Ser | Thr | His | Pro | Asp | Leu | Asn | Ile | Arg | Gly | Gly | Ala | Ser |
| | | 35 | | | | | 40 | | | | | 45 | | | |
| Phe | Val | Pro | Gly | Glu | Pro | Ser | Thr | Gln | Asp | Gly | Asn | Gly | His | Gly | Thr |
| | 50 | | | | | 55 | | | | | 60 | | | | |
| His | Val | Ala | Gly | Thr | Ile | Ala | Ala | Leu | Asn | Asn | Ser | Ile | Gly | Val | Leu |
| 65 | | | | | 70 | | | | | 75 | | | | | 80 |
| Gly | Val | Ala | Pro | Ser | Ala | Glu | Leu | Tyr | Ala | Val | Lys | Val | Leu | Gly | Ala |
| | | | | 85 | | | | | 90 | | | | | 95 | |
| Ser | Gly | Ser | Gly | Ser | Val | Ser | Ser | Ile | Ala | Gln | Gly | Leu | Glu | Trp | Ala |
| | | | 100 | | | | | 105 | | | | | 110 | | |
| Gly | Asn | Asn | Gly | Met | His | Val | Ala | Asn | Leu | Ser | Leu | Gly | Ser | Pro | Ser |
| | | 115 | | | | | 120 | | | | | 125 | | | |
| Pro | Ser | Ala | Thr | Leu | Glu | Gln | Ala | Val | Asn | Ser | Ala | Thr | Ser | Arg | Gly |
| | 130 | | | | | 135 | | | | | 140 | | | | |
| Val | Leu | Val | Val | Ala | Ala | Ser | Gly | Asn | Ser | Gly | Ala | Gly | Ser | Ile | Ser |
| 145 | | | | | 150 | | | | | 155 | | | | | 160 |
| Tyr | Pro | Ala | Arg | Tyr | Ala | Asn | Ala | Met | Ala | Val | Gly | Ala | Thr | Asp | Gln |
| | | | | 165 | | | | | 170 | | | | | 175 | |
| Asn | Asn | Asn | Arg | Ala | Ser | Phe | Ser | Gln | Tyr | Gly | Ala | Gly | Leu | Asp | Ile |
| | | | 180 | | | | | 185 | | | | | 190 | | |
| Val | Ala | Pro | Gly | Val | Asn | Val | Gln | Ser | Thr | Tyr | Pro | Gly | Ser | Thr | Tyr |
| | | 195 | | | | | 200 | | | | | 205 | | | |
| Ala | Ser | Leu | Asn | Gly | Thr | Ser | Met | Ala | Thr | Pro | His | Val | Ala | Gly | Ala |
| | 210 | | | | | 215 | | | | | 220 | | | | |
| Ala | Ala | Leu | Val | Lys | Gln | Lys | Asn | Pro | Ser | Trp | Ser | Asn | Val | Gln | Ile |
| 225 | | | | | 230 | | | | | 235 | | | | | 240 |
| Arg | Asn | His | Leu | Lys | Asn | Thr | Ala | Thr | Ser | Leu | Gly | Ser | Thr | Asn | Leu |
| | | | | 245 | | | | | 250 | | | | | 255 | |
| Tyr | Gly | Ser | Gly | Leu | Val | Asn | Ala | Glu | Ala | Ala | Thr | Arg | | | |
| | | | 260 | | | | | 265 | | | | | | | |

We claim:

1. A substantially pure stabilized subtilisin, in which the amino acid proline is substituted for a naturally occurring amino acid and which position(s) is/are not located in regions, in which the protease is characterized by possessing α-helical or β-sheet structure.

2. The stabilized subtilisin of claim 1 wherein the dihedral angles constitute values within the intervals $-90°<\phi<-40°$ and $120°<\psi<180°$.

3. The stabilized subtilisin of claim 1 wherein the dihedral angles constitute values within the intervals $-90°<\phi<40°$ and $-50°<\psi<10°$.

4. The subtilisin of claim 1, further comprising one or more of the following BPN substitutions: 27R, 36D, 97N, 98R, 188P, 194P, 120D, 128G, 195E, 235L, 235R, 237R, 251E, and 263F.

5. The subtilisin of claim 1, selected from the group consisting of: a stabilized subtilisin 309, a stabilized subtilisin 147, a stabilized subtilisin BPN', and a stabilized subtilisin Carlsberg.

6. The stabilized subtilisin 309 of claim 5 having one or more proline substitutions at positions numbered according to their alignment with the analogous amino acid position in the amino acid sequence of the mature subtilisin BPN selected from the group consisting of other than proline at one or more positions selected from the group consisting of 38, 57, 98, 172, 242 and 259, said positions numbered according to their alignment with the analogous amino acid position in the amino acid sequence of the mature subtilisin BPN, wherein the naturally occurring amino acid to be substituted at said one or more positions has values for the dihedral angles φ (phi) and ψ (psi) within the interval −90°<φ<−40° and within the interval −180°<ψ<180° T38P, S57P, A98P, A172P, S188P, A194P, S242P, and S259P.

7. Subtilisin 309 of claim 6, further comprising one or more of the following BPN substitutions: K27R, *36D, N76D, G97N, A98R, V104Y, H120D, S128G, G195E, Q206C, N218S, K235L, K235R, K237R, K251E, and Y263F.

8. A substantially pure, stabilized, subtilisin 309 having the following amino acid substitutions at positions numbered according to their alignment with the analogous amino acid position in the amino acid sequence of the mature subtilisin BPN K27R+*36D+G97N+A98R+A194P+K235R+K237R+K251E+Y263F.

9. A substantially pure, stabilized, subtilisin 309 having the following amino acid substitutions at positions numbered according to their alignment with the analogous amino acid position in the amino acid sequence of the mature subtilisin BPN K27R+*36D+G97N+A194P+K235R+K237R+K25 E+Y263F.

10. A substantially pure, stabilized, subtilisin 309 having the following amino acid substitutions at positions numbered according to their alignment with the analogous amino acid position in the amino acid sequence of the mature subtilisin BPN K27R+*36D+G97N+A194P+K235R+K237R+Y263F.

11. A substantially pure, stabilized, subtilisin 309 having the following amino acid substitutions at positions numbered according to their alignment with the analogous amino acid position in the amino acid sequence of the mature subtilisin BPN *36D+G97N+V104Y+H120D+A194P+G195E.

12. A substantially pure, stabilized, subtilisin 309 having the following amino acid substitutions at positions numbered according to their alignment with the analogous amino acid position in the amino acid sequence of the mature subtilisin BPN *36D+G97N+v104Y+H120D+A194P+G195E+K235L.

13. A substantially pure, stabilized, subtilisin 309 having the following amino acid substitutions at positions numbered according to their alignment with the analogous amino acid position in the amino acid sequence of the mature subtilisin BPN *36D+G97N+H120D+A194P+G195E.

14. A substantially pure, stabilized, subtilisin 309 having the following amino acid substitutions at positions numbered according to their alignment with the analogous amino acid position in the amino acid sequence of the mature subtilisin BPN *36D+G97N+H120D+Al94P+G195E+K235L.

15. A substantially pure, stabilized, subtilisin 309 having the following amino acid substitutions at positions numbered according to their alignment with the analogous amino acid position in the amino acid sequence of the mature subtilisin BPN *36D+V104Y+H120D+A194P+G195E.

16. A substantially pure, stabilized, subtilisin 309 having the following amino acid substitutions at positions numbered according to their alignment with the analogous amino acid position in the amino acid sequence of the mature subtilisin BPN *36D+V104Y+H120D+A194P+G195E+K235L.

17. A nucleotide sequence encoding a stabilized protease of claim 1.

18. An expression vector comprising a nucleotide sequence encoding a stabilized protease according to claim 1.

19. A host organism containing an expression vector carrying a nucleotide sequence encoding a stabilized protease of claim 1.

* * * * *

UNITED STATES PATENT AND TRADEMARK OFFICE
CERTIFICATE OF CORRECTION

PATENT NO. : 5,858,757
DATED : January 12, 1999
INVENTOR(S) : Von Der Osten et al.

It is certified that error appears in the above-identified patent and that said Letters Patent is hereby corrected as shown below:

ON THE TITLE PAGE

Foreign Application Priority Data: Delete "91610036", insert --91610036.5--

IN THE CLAIMS:

Column 25, line 57: after "and", insert --other than proline at one or more positions selected from the group consisting of 38, 57, 98, 172, 242 and 259, said positions numbered according to their alignment with the analogous amino acid position in the amino acid sequence of the mature subtilisin BPN, wherein the naturally occurring amino acid to be substituted at said one or more positions has values for the dihedral angles $\Phi$ (phi) and $\Psi$ (psi) within the intervals $-90° < \Phi < -40°$ and within the interval $-180° < \Psi < 180°$--

Column 25, line 64: delete "$< 40°$", insert --$< -40°$--

UNITED STATES PATENT AND TRADEMARK OFFICE
CERTIFICATE OF CORRECTION

PATENT NO. : 5,858,757
DATED : January 12, 1999
INVENTOR(S) : Von Der Osten et al.

It is certified that error appears in the above-identified patent and that said Letters Patent is hereby corrected as shown below:

IN THE CLAIMS:

Column 26, line 56: delete "1", insert --4--

Column 26, lines 64-67: delete "other than proline at one or more positions selected from the group consisting of 38, 57, 98, 172, 242 and 259, said positions numbered according to their alignment with the analogous amino acid"

Column 27, lines 1-5: delete "position in the amino acid sequence of the mature subtilisin BPN, wherein the naturally occurring amino acid to be substituted at said one or more positions has values for the dihedral angles Φ (phi) and Y (psi) within the intervals -90° < Φ < -40° and within the interval -180° < Y < 180°"

Column 27, line 23: delete "K25 E+", insert --K251E+--

Signed and Sealed this

Seventeenth Day of April, 2001

NICHOLAS P. GODICI

Attest:

Attesting Officer

Acting Director of the United States Patent and Trademark Office